(12) United States Patent
Szczepankiewicz et al.

(10) Patent No.: US 10,316,054 B2
(45) Date of Patent: Jun. 11, 2019

(54) PREPARATION AND USE OF CRYSTALLINE BETA-D-NICOTINAMIDE RIBOSIDE

(71) Applicant: GlaxoSmithKline Intellectual Property (No. 2) Limited, Brentford, Middlesex (GB)

(72) Inventors: Bruce G. Szczepankiewicz, Hopkinton, MA (US); Karsten Koppetsch, Woburn, MA (US); Robert B. Perni, Marlborough, MA (US)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 15/315,068

(22) PCT Filed: Jun. 2, 2015

(86) PCT No.: PCT/IB2015/054181
§ 371 (c)(1),
(2) Date: Nov. 30, 2016

(87) PCT Pub. No.: WO2015/186068
PCT Pub. Date: Dec. 10, 2015

(65) Prior Publication Data
US 2017/0204131 A1    Jul. 20, 2017

Related U.S. Application Data

(60) Provisional application No. 62/006,434, filed on Jun. 2, 2014.

(51) Int. Cl.
*A01N 43/04* (2006.01)
*A61K 31/70* (2006.01)
*C07H 19/048* (2006.01)
*C07H 1/00* (2006.01)
*C07H 1/06* (2006.01)

(52) U.S. Cl.
CPC ............ *C07H 19/048* (2013.01); *C07H 1/00* (2013.01); *C07H 1/06* (2013.01); *C07B 2200/13* (2013.01)

(58) Field of Classification Search
None
See application file for complete search history.

(56) References Cited

FOREIGN PATENT DOCUMENTS

WO    WO 2015/014722 A1    2/2015
WO    WO 2015/066382 A1    5/2015

OTHER PUBLICATIONS

Jarman et al. J. Chem. Soc. (C) (1969), pp. 199-203.*
Khan et al. EMBO Molecular Medicine (2014), vol. 6, pp. 721-731.*
Tianle Yang, "Syntheses of Nicotinamide Riboside and Derivatives: Effective Agents for Increasing Nicotinamide Adenine Dinucleotide Concentrations in Mammalian Cells", J. Med. Chem. 2007, vol. 50, pp. 6458-6461.
Shinji Tanimori, "An Efficient Chemical Synthesis of Nicotinamide Riboside (NAR) and Analogues", Bioorganics & Medicinal Chemistry Letters, vol. 12, 2002, pp. 1135-1135.

* cited by examiner

*Primary Examiner* — Patrick T Lewis
(74) *Attorney, Agent, or Firm* — Diane E. Furman; Joshua C. Sanders

(57) ABSTRACT

Provided herein are crystalline beta-D-nicotinamide riboside chloride compositions and methods of preparation and use thereof. Also provided are related pharmaceutical compositions and methods of use thereof. The crystalline beta-D-nicotinamide riboside chloride compositions may be used to treat a disease or disorder that would benefit from increased NAD levels including a mitochondrial disease or disorder, insulin resistance, a metabolic syndrome, diabetes, obesity, or for increasing insulin sensitivity in a subject.

20 Claims, 16 Drawing Sheets common numbering scheme

PREPARATION AND USE OF CRYSTALLINE BETA-D-NICOTINAMIDE RIBOSIDE

This application is a § 371 of International Application No. PCT/IB2015/054181, filed 2 Jun. 2015, which claims the benefit of U.S. Provisional Application No. 62/006,434, filed 2 Jun. 2014, which are incorporated herein in their entireties.

BACKGROUND

In the early part of the $20^{th}$ century, vitamin $B_3$ was identified as a component missing from the diet of pellagra patients. Supplementation with nicotinic acid, or niacin, ameliorated the symptoms of pellagra, and prevented the onset of this condition in areas where it was prevalent. The biochemical role of niacin was elucidated in the 1930s, when it was found to be critical for the biosynthesis of nicotinamide adenine dinucleotide (NAD), a compound essential for cellular respiration (Preiss, J.; Handler, P. Biosynthesis of Diphosphopyridine Nucleotide I. Identification of Intermediates J. Biol. Chem. 1958 233, 488-492; Preiss, J.; Handler, P. Biosynthesis of Diphosphopyridine Nucleotide II. Enzymatic Aspects J. Biol. Chem. 1958 233, 493-500). The precise role of NAD in cellular respiration is well understood. As glucose and fatty acids are oxidized, NAD can accept a hydride equivalent, which results in its reduction to NADH. NADH can donate a hydride equivalent, resulting in oxidation back to NAD. These reduction-oxidation cycles use NAD for the temporary storage of hydride ion, but they do not consume NAD. There are other enzymes that use NAD in a different manner, and for purposes not directly related to energy production. Poly-ADPribose polymerases (PARPs), ADPribose transferases (ARTs), and sirtuins all catalyze reactions that release nicotinamide from NAD. This reaction generates a significant amount of energy, similar to ATP hydrolysis. The reverse reaction does not occur readily, so NAD must be replenished by other mechanisms (Bogan, K. L.; Brenner, C. Nicotinic Acid, Nicotinamide, and Nicotinamide Riboside: A Molecular Evaluation of NAD+ Precursor Vitamins in Human Nutrition *Annu. Rev. Nutr.* 2008, 28, 115-130).

Niacin (or nicotinic acid (pyridine-3-carboxylic acid)), and its amide niacinamide (or nicotinamide (pyridine-3-carboxamide)) are converted to NAD in vivo. In mammals, niacinamide, rather than niacin, may be the major NAD precursor. The set of biosynthetic transformations from niacinamide to NAD is shown in FIG. 1. The rate limiting step for this pathway is the formation of the bond between niacinamide and 5-phosphoribose-1-pyrophosphate (PRPP), and it is catalyzed by nicotinamide phosphoribosyl transferase (NAMPT) (Revollo, J. R.; Grimm, A. A.; Imai, S.-I. J. Biol. Chem. 2004, 279, 50754-50763). The NAMPT pathway is thought to be the most efficient route known for nicotinamide recycling. Niacin enters into a similar set of transformations, but in a final step, the carboxylic acid must be converted to a carboxamide to produce NAD. The biosynthesis of NAD from niacin follows the Preiss-Handler pathway (FIG. 1).

In 1982, nicotinamide riboside (NR) was investigated as a NAD precursor in prokaryotes (Liu, G.; Foster, J.; Manlapaz-Ramos, R.; Loivera, B. M. "Nucleoside Salvage Pathway for NAD Biosynthesis in Salmonella typhimurium" *J. Bacteriol.* 1982, 152, 1111-1116). In contrast to niacin, exogenously supplied NR is hypothesized to bypass the first and most energy-consuming part of both the Preiss-Handler pathway and the NAMPT pathway (FIG. 1). Although NR appears to be a natural precursor for NAD, it likely contributes only a small amount to NAD biosynthesis owing to the apparent scarcity of NR in dietary sources. NR contains a high energy glycosidic bond that is spontaneously labile in aqueous solution, yielding nicotinamide and ribose decomposition products. This spontaneous reaction occurs over the course of hours or days depending on the exact ambient conditions, but it makes any naturally occurring NR difficult to keep in food sources, while nicotinic acid or nicotinamide are considerably more stable and easy to prepare and administer. NR has been reported to occur in milk (Bieganowski and Brenner (2004) Cell 117: 495-502) and beer, but the amounts typically present are probably too small to be nutritionally significant.

Currently, NR supplementation is limited by the available commercial supply. NR supplementation could represent a dietary alternative to niacin, with the advantage of being a more efficient NAD precursor. By taking advantage of a natural pathway to synthesize NAD while consuming less energy, NR could offer benefits for human health. Cells are constantly subject to damage by normal environmental factors, and they have evolved repair mechanisms to continuously reverse this damage. The repair mechanisms consume NAD by scission of the high energy glycosidic linkage to produce species such as poly-ADPribose and ADP-ribosylated proteins. In severely damaged cells, energy stores are not sufficient to produce the NAD necessary to maintain homeostasis, and the damage becomes irreversible. Therefore, an energy-rich NAD precursor such as NR may be able to address cell and tissue damage at the molecular level.

NR is difficult to isolate from natural sources, so it is almost always produced by chemical synthesis. The first chemical synthesis was accomplished by Todd and co-workers in 1957 (Haynes, L. J.; Hughes, N. A.; Kenner, G. W.; Todd, A. *J. Chem. Soc.* 1957, 3727-3732). This group produced NR chloride as α mixture of a and β anomers about the glycosidic linkage in an approximately 1:4 ratio. The product was described as a hygroscopic oil that could not be crystallized. Other investigators who isolated NR chloride from biochemical sources also described it as a hygroscopic oil (Schlenk, F. "Nicotinamide Nucleoside" *Natunviss.* 1940, 28, 46-47; Gingrich, W.; Schlenk, F. "Codehydrogenase I and Other Pyridinium Compounds as V-Factor for Hemophilus Influenzae and H. Parainfluenzae" *J. Bacteriol.* 1944, 47, 535-550). Significantly, biochemical syntheses should have produced only the natural β-anomer, though the exact stereochemical arrangement was not determined. Later reports confirmed the hygroscopic, amorphous nature of NR chloride (Jarman, M.; Ross, W. C. J. *J. Chem. Soc.* C, 1969, 199-203; and Atkinson, M. R.; Morton, R. K.; Naylor, R. Synthesis of Glycosylpyridinium Compounds from Glycosylamines and from Glycosyl Halides *J. Chem Soc.* 1965, 610-615). Other groups investigated alternative NR anions. One synthesis described the anomerically pure NR bromide salt as crystalline, but the product was not adequately described to ascertain whether the material was truly crystalline or merely an amorphous solid (Lee, J.; Churchill, H.; Choi, W.-B.; Lynch, J. E.; Roberts, F. E.; Volante, R. P.; Reider, P. J. "A chemical synthesis of nicotinamide adenine dinucleotide ($NAD^+$)" Chem. Commun. 1999, 729-730). Subsequently, other NR salts were prepared and solids were obtained, though they were never described as crystalline (Tanimori, S.; Ohta, T.; Kirihata, M. An Efficient Chemical Synthesis of Nicotinamide Riboside (NAR) and Analogues *Bioorg. Med. Chem. Lett.* 2002, 12, 1135-1137; Franchetti, P.; Pasqualini, M.; Petrelli, R.; Ricciutelli, M.; Vita, P.; Cappellacci, L. *Bioorg. Med. Chem. Lett.* 2004, 14, 4655-4658; Yang, T.; Chan, N. Y.-K.; Sauve, A. A. *J. Med. Chem.* 2007, 50, 6458-6461).

Previously described NR salt preparations are amorphous NR and extremely hygroscopic, becoming sticky solids within seconds or minutes and collapsing to oils within hours at ambient temperature and humidity. Maintaining the amorphous salts as solids required storing them under a dry atmosphere, or keeping them frozen at approximately −20° C. Importantly, the oily mixtures decomposed significantly over the course of one day at ambient temperature. This property presents a major challenge for isolating and handling NR salts. It also makes it difficult to specify the purity of an NR preparation, because some handling under ambient conditions is inevitable during analysis or use. Ease of handling and purity are important parameters for a substance that might be manufactured for human consumption. These are also important considerations for a substance that will be used for any subsequent purpose, for example as a synthetic intermediate for another chemical transformation, as a biochemical reagent, as an analytical standard, or for any other use where chemical purity and stability are desired.

Furthermore, while several of the previously described preparations of anomerically pure NR salt crystals have been bromide rather than chloride salts, bromide salts may be unnecessarily toxic or otherwise undesireable as a pharmaceutical salt form compared to corresponding chloride salts. For example, bromide compounds, especially potassium bromide, was frequently used as sedatives in the 19th and early 20th century, but their use in over-the-counter sedatives and headache remedies (such as Bromo-Seltzer) ended in the United States in 1975, when bromides were withdrawn due to chronic toxicity. Doses of 0.5-1 gram per day of bromide can lead to bromism, a syndrome with multiple neurological symptoms and skin eruptions (see Olson, Kent R. (1 Nov. 2003). Poisoning & drug overdose (4th ed.) Appleton & Lange. pp. 140-141). In contrast, chloride is considered a "first class" pharmaceutical salt-former that can be used more or less without restriction as it represents a physiologically ubiquitous ion, and, indeed, healthy adults are even encouraged to consume 2.3 grams of chloride each day to replace the amount lost daily on average through sweat and to achieve a diet that provides sufficient amounts of other essential nutrients (see, Saal, C.; Becker, A. *Eur J Pharm Sci* 2013, 49(4), 614-623; and Institute of Medicine of the National Academies, 2013, Dietary reference intakes: water, potassium, sodium, chloride, and sulfate, from the Institute of Medicine of the National Academies:<http://www.iom.edu/Reports/2004/Dietary-Reference-Intakes-Water-Potassium-Sodium-Chloride-and-Sulfate. Therefore chloride pharmaceutical salts are generally safer than corresponding bromide salt forms, particularly for pharmaceutical salts that require relatively high dosages.

Accordingly, there is a need for a chemically pure and stable form of a pharmaceutically acceptable NR salt such as nicotinamide riboside chloride, as well as for corresponding methods for its synthesis and efficient preparation on a large scale.

SUMMARY

The present invention describes the preparation and characterization of two distinct crystalline forms of nicotinamide riboside chloride. In one embodiment, nicotinamide riboside chloride crystallizes to give a substance that contains nicotinamide riboside chloride with less than 5000 ppm other substances, especially ethanol (for example, a nicotinamide riboside chloride crystal of greater than 90% purity (w/w) having <4000 ppm ethanol and <1000 ppm other solvents). In a second embodiment, nicotinamide riboside chloride crystallizes to give a substance that contains 0.9 molar equivalent of methanol per 1 equivalent of nicotinamide riboside chloride (for example, a nicotinamide riboside chloride crystal of greater than 90% purity (w/w) having less than 1.1 molar equivalent of methanol, e.g., 0.01 to 1.0 molar equivalent of methanol, and <1000 ppm other solvents). Both of these substances reflect and refract plane polarized light such that they are visible through a polarized light filter, while the background is dark. Both crystalline forms are stable for at least four weeks under ambient storage conditions. In certain embodiments, the crystalline form is stable for at least six weeks, eight weeks, two months, four months, eight months or twelve months. In certain embodiments, ambient storage conditions are the commonly referenced standard ambient temperature and pressure (SATP), which is 25° C. (77° F.), and a pressure of 100 kPA (~1 atm, 14.7 psi). Alternatively, ambient conditions are the IUPAC (International Union of Pure and Applied Chemistry) standard conditions for tempertature and pressure, such as a temperature of 0° C. (32° F.), and a pressure of 100 kPA (~1 atm, 14.7 psi).

Additionally, the first crystal form is far more resistant to decomposition upon heating than amorphous forms of nicotinamide riboside. The crystalline nature of the material offers a tremendous advantage over the previously described oily or amorphous forms in terms of its chemical stability and purity. Both crystal forms are composed of >95% pure nicotinamide riboside chloride, excluding the methanol present in the second embodiment. The crystalline forms also make manipulation of the bulk material much easier than handling of the amorphous forms.

The present invention also describes a method for preparing nicotinamide riboside chloride that is amenable to large-scale synthesis. In the method, no chromatography is employed for the isolation of any intermediate. Ion exchange from trifluoromethanesulfonate or acetate to chloride is accomplished by extraction of an aqueous solution containing nicotinamide riboside, sodium chloride and an alkali metal trifluoromethanesulfonate salt with an organic solvent, especially tetrahydrofuran. This ion exchange method circumvents the need for ion exchange resins or cumbersome chromatography to prepare the chloride salt. The ability to prepare nicotinamide riboside chloride on a large scale makes it possible to prepare nicotinamide riboside for use as a food additive, as a nutritional supplement, as an intermediate for chemical synthesis, or for any other purpose where large quantities, e.g. >1 g, of nicotinamide riboside chloride would be useful.

Nicotinamide riboside chloride, especially >95% pure β-nicotinamide riboside chloride, represents a desirable salt form for human consumption. The chloride anion is generally recognized as safe, without any obvious toxicity or undesirable pharmacological effects. This stands in contrast to the bromide salt form of nicotinamide riboside previously disclosed, as bromide salts are known to have unwanted and potentially dangerous neurological effects (Friedlander, W. J. *Arch. Neurol.* 2000, 57, 1782-1785). Sulfate and phosphate anions have laxative properties (Patel, V.; Nicar, M.; Emmett, M.; Asplin, J.; Maguire, J. A.; Santa Ana, C. A.; Fordtran, J. S. *Am. J. Gastroenterol.* 2009, 104, 953-965). Iodide is known to decrease the production of thyroxin and has metabolic effects that must be carefully monitored (Büurgi, H. *Best Pract. Res. Clin. Endocrinol. Metab.* 2010, 24, 107-115). Carboxylates are known to react with the glycosidic bond of NR, so chemical purity of the final compound is more difficult to ensure with these anions than with the chloride salt (Szczepankiewicz, B. G.; Koppetsch, K. J.; Perni, R. B. *J. Org. Chem.* 2011, 76, 6465-6474). Other anions, such as methanesulfonate, toluenesulfonate, trifluoromethanesulfonate, perchlorate, tetrafluoroborate, hexafluorophosphate, and a large variety of others introduce a foreign component when given to humans, as this class of anions represents chemical species not normally present in the body.

In the present invention, chloride is the preferred counterion for nicotinamide riboside. However, the methods of the invention may be adapted to produce salt forms such as di(nicotinamide riboside) sulfate, nicotinamide riboside hydrogensulfate, mono- or di-(nicotinamide riboside) phosphate, mono-, di-, tri-, or tetra-nicotinamide riboside carboxylates (including acetate, propionate, butyrate, and other monocarboxylates, as well as malonate, succinate, fumarate, maleate and other dicarboxylates, citrate, isocitrate and other tricarboxylates, ethylenediaminetetraacetate and other tetracarboxylates), nicotinamide riboside iodide, nicotinamide riboside methanesulfonate, nicotinamide riboside toluenesulfonate, nicotinamide riboside trifluoromethanesulfonate, nicotinamide riboside perchlorate, nicotinamide riboside bicarbonate, di(nicotinamide riboside) carbonate, or any other nicotinamide riboside salt which are less preferred forms than nicotinamide riboside chloride.

In one aspect, the invention provides a substantially isomerically pure 3-carbamoyl-1-((2R,3R,4S,5R)-3,4-dihydroxy-5 (hydroxymethyl)tetrahydrofuran-2-yl)pyridin-1-ium (β-D-nicotinamide riboside (or 2R (β) nicotinamide riboside)) chloride crystal of greater than 90% chemical purity (w/w) containing <4000 ppm ethanol and <1000 ppm other solvents.

In a further aspect, the invention provides a substantially isomerically pure 3-carbamoyl-1-((2R,3R,4S,5R)-3,4-dihydroxy-5 (hydroxymethyl)tetrahydrofuran-2-yl)pyridin-1-ium (β-D-nicotinamide riboside (or 2R (β) nicotinamide riboside)) chloride methanolate crystal of greater than 90% chemical purity (w/w) containing between 0.01 and 1.1 molar equivalent of methanol and <1000 ppm other solvents. In one embodiment, the substantially isomerically pure 3-carbamoyl-1-((2R,3R,4S,5R)-3,4-dihydroxy-5 (hydroxymethyl)tetrahydrofuran-2-yl)pyridin-1-ium (β-D-nicotinamide riboside) chloride methanolate crystal of claim 2 containd between 0.7 and 1.1 molar equivalent of methanol.

In certain embodiments of the invention, the substantially pure β-D-nicotinamide riboside (2R (β) nicotinamide riboside) chloride crystal comprises less than 1% (mol/mol) of 3-carbamoyl-1-((2S,3R,4S,5R)-3,4-dihydroxy-5 (hydroxymethyl)tetrahydrofuran-2-yl) pyridin-1-ium (2S (α) nicotinamide riboside) chloride.

In further embodiments of the invention, the substantially isomerically pure β-D-nicotinamide riboside (2R ((β) nicotinamide riboside) chloride crystal has a chemical purity of greater than 95% (w/w). In certain embodiments, the substantially isomerically pure β-D-nicotinamide riboside (2R ((β) nicotinamide riboside) chloride crystal has a chemical purity greater than or equal to 99% (w/w). In certain embodiments, the substantially isomerically pure β-D-nicotinamide riboside (2R (β) nicotinamide riboside) chloride crystal contains <4000 ppm ethanol. In particular embodiments, the substantially isomerically pure 13-D-nicotinamide riboside (2R (β) nicotinamide riboside) chloride crystal contains a level of ethanol that is, for example, between 0 and 100 ppm ethanol, or between 100 and 200 ppm ethanol, or between 200 and 300 ppm ethanol, or between 300 and 400 ppm ethanol, or between 400 and 500 ppm ethanol.

In particular embodiments, the substantially isomerically pure β-D-nicotinamide riboside (2R (β) nicotinamide riboside) chloride crystal of has an X-ray powder diffraction pattern substantially as shown in FIG. 6 (for example, an X-ray powder diffraction pattern having four or more of the following X-ray powder diffraction peaks: about 14.2, about 17.1, about 20.5, about 22.7, about 23.8, about 25.1, about 26.8, and about 34.2 degrees).

In further embodiments, the substantially isomerically pure β-D-nicotinamide riboside (2R ((β) nicotinamide riboside) chloride crystal has an infrared absorption spectrum substantially as shown in FIG. 8 (for example, an infrared absorption spectrum comprising peaks at approximately (cm$^{-1}$) 3299, 1700, 1398, 1080, 982, 887, and 795).

In certain embodiments, the substantially isomerically pure β-D-nicotinamide riboside (2R ((β) nicotinamide riboside) chloride methanolate crystal has an X-ray powder diffraction pattern substantially as shown in FIG. 4 (for example, an X-ray powder diffraction pattern having five or more of the following X-ray powder diffraction peaks: about −11.1, about −7.1, about −2.9, about 1.0, about 4.7, about 15.2, about 18.2, about 21.4, about 23.5, about 24.9, about 26.0, and about 27.7 degrees.

In further embodiments, the substantially isomerically pure β-D-nicotinamide riboside (2R ((β) nicotinamide riboside) methanolate crystal has an infrared absorption spectrum substantially as shown in FIG. 7 (for example, an infrared absorption spectrum substantially comprising peaks at approximately (cm$^{-1}$) 3361, 1674, 1610, 1394, 1082, 982, 833, and 792).

In another aspect, the invention provides a method of obtaining a substantially isomerically pure β-D-nicotinamide riboside (2R ((β) nicotinamide riboside) chloride crystal, wherein an organic solvent is used to extract a trifluoromethanesulfonate salt from an aqueous reaction mixture into the organic solvent resulting in removal of the trifluoromethanesulfonate anion from the aqueous mixture. In certain embodiments, the organic solvent is an ethereal solvent. In particular embodiments, the ethereal solvent is tetrahydrofuran, 2-methyltetrahydrofuran, 3-methyltetrahydrofuran, pyran, dioxane, 1,2-dimethoxyethane, 1,2-diethoxyethane, diethyl ether, di-n-propyl ether, diisopropyl ether, or tert-butyl methyl ether. In further embodiments, the organic solvent is acetonitrile, propionitrile, or butyronitrile. In still further embodiments, the organic solvent is tetrahydrofuran, 2-methyltetrahydrofuran, or acetonitrile. In other embodiments, the trifluoromethanesulfonate salt is lithium trifluoro-methanesulfonate, sodium trifluoromethanesulfonate, potassium trifluoromethanesulfonate, rubidium trifluoromethanesulfonate, cesium trifluoromethanesulfonate, ammonium trifluoro-methanesulfonate, calcium trifluoromethanesulfonate, or magnesium trifluoromethanesulfonate.

In another aspect, the invention provides a pharmaceutical composition comprising a substantially isomerically pure 3-carbamoyl-1-((2R,3R,4S,5R)-3,4-dihydroxy-5 (hydroxymethyl)tetrahydrofuran-2-yl)pyridin-1-ium (β-D-nicotinamide riboside (or 2R (β) nicotinamide riboside)) chloride crystal of greater than 90% chemical purity (w/w) containing <4000 ppm ethanol and <1000 ppm other solvents. In certain embodiments, the pharmaceutical composition is for enteral administration. In particular embodiments, the pharmaceutical composition is for oral administration. In further embodiments, the pharmaceutical composition is for rectal or sublingual administration. In other embodiments, the pharmaceutical composition is for parenteral administration. In still other embodiments, the pharmaceutical composition is for intravenous injection. In still other embodiments, the pharmaceutical composition is for intranasal, dermal, urogenital, ophthalmic, otologic, or respiratory inhalation administration.

In another aspect, the invention provides a food or beverage fit for consumption by a mammal comprising a substantially isomerically pure 3-carbamoyl-1-((2R,3R,4S,5R)-3,4-dihydroxy-5 (hydroxymethyl)tetrahydrofuran-2-yl)pyridin-1-ium (β-D-nicotinamide riboside (or 2R ((β) nicotinamide riboside)) chloride crystal of greater than 90% chemical purity (w/w) containing <4000 ppm ethanol and <1000 ppm other solvents. In certain embodiments, the food or beverage comprises at least about 10 mg of nicotinamide riboside per kilogram of food or beverage. In particular embodiments, the food or beverage comprises at least about 10 mg of nicotinamide riboside per gram of food or beverage.

In still another aspect, the invention provides a method of preparing a pharmaceutically acceptable non-chloride salt form of 3-carbamoyl-1-((2R,3R,4S,5R)-3,4-dihydroxy-5-(hydroxymethyl)tetrahydrofuran-2-yl)pyridin-1-ium (β-D-nicotinamide riboside or 2R (β) nicotinamide riboside) cation by providing crystalline 3-carbamoyl-1-((2R,3R,4S,5R)-3,4-dihydroxy-5-(hydroxymethyl)tetrahydrofuran-2-yl)pyridin-1-ium (β-D-nicotinamide riboside (2R (β) nicotinamide riboside)) chloride, and chemically processing it to provide the pharmaceutically acceptable non-chloride salt form of 3-carbamoyl-1-((2R,3R,4S,5R)-3,4-dihydroxy-5-(hydroxymethyl)-tetrahydrofuran-2-yl)pyridin-1-ium (β-D-nicotinamide riboside (2R (β) nicotinamide riboside)) cation salt. In certain embodiments, the crystalline 3-carbamoyl-1-((2R,3R,4S,5R)-3,4-dihydroxy-5-(hydroxymethyl)tetrahydrofuran-2-yl)pyridin-1-ium (2R (β) nicotinamide riboside) chloride is a substantially isomerically pure 3-carbamoyl-1-((2R,3R,4S,5R)-3,4-dihydroxy-5 (hydroxymethyl)tetrahydrofuran-2-yl)pyridin-1-ium (β-D-nicotinamide riboside (or 2R (β) nicotinamide riboside)) chloride crystal of greater than 90% chemical purity (w/w) containing <4000 ppm ethanol and <1000 ppm other solvents. In other embodiments, the crystalline 3-carbamoyl-1-((2R,3R,4S,5R)-3,4-dihydroxy-5-(hydroxymethyl)tetrahydrofuran-2-yl)pyridin-1-ium (2R (13) nicotinamide riboside) chloride is a substantially isomerically pure 3-carbamoyl-1-((2R,3R,4S,5R)-3,4-dihydroxy-5 (hydroxymethyl)tetrahydrofuran-2-yl)pyridin-1-ium (13-D-nicotinamide riboside (or 2R (β) nicotinamide riboside)) chloride methanolate crystal of greater than 90% chemical purity (w/w) containing between 0.01 and 1.1 molar equivalent of methanol and <1000 ppm other solvents. In further embodiments, the pharmaceutically acceptable non-chloride cation is sulfate, phosphate, methanesulfonate, ethanesulfonate, toluenesulfonate, acetate, propionate, butyrate, isobutyrate, pentanoate, hexanoate, heptanoate, octanoate, lactate, 2-hydroxybutyrate, 3-hydroxybutyrate, benzoate, malonate, succinate, fumarate, maleate, malate, citrate, isocitrate, or ethylenediamine-tetraacetate.

In yet another aspect, the invention provides a method of preparing an aqueous solution of 3-carbamoyl-1-((2R,3R,4S,5R)-3,4-dihydroxy-5-(hydroxymethyl) tetrahydrofuran-2-yl)pyridin-1-ium (2R (β) nicotinamide riboside) chloride by providing a crystalline 3-carbamoyl-1-((2R,3R,4S,5R)-3,4-dihydroxy-5-(hydroxymethyl) tetrahydrofuran-2-yl) pyridin-1-ium (2R (β) nicotinamide riboside) chloride, and contacting the crystalline 2R (β) nicotinamide riboside chloride with water.

In other aspects, the invention provides a method of treating a disease or disorder that would benefit from increased NAD levels comprising administering a pharmaceutical composition comprising a β-D-nicotinamide riboside (2R (β) nicotinamide riboside) chloride crystal, wherein the β-D-nicotinamide riboside (2R (β) nicotinamide riboside) chloride crystal is a substantially isomerically pure 3-carbamoyl-1-((2R,3R,4S,5R)-3,4-dihydroxy-5 (hydroxymethyl)tetrahydrofuran-2-yl)pyridin-1-ium (β-D-nicotinamide riboside (or 2R (β) nicotinamide riboside)) chloride crystal of greater than 90% chemical purity (w/w) containing <4000 ppm ethanol and <1000 ppm other solvents. In certain embodiments, the disease or disorder is insulin resistance, a metabolic syndrome, diabetes, or obesity. In particular embodiments, the disease or disorder is a mitochondrial disease or disorder. In certain embodiments, the mitochondrial disease or disorder is a neuromuscular disorder, a disorder of neuronal instability, a neurodegenerative disorder, or a mitochondrial myopathy. In further embodiments, the mitochondrial disease or disorder is Friedreich's Ataxia, muscular dystrophy, multiple sclerosis, seizure disorders, migraine, Alzheimer's Disease, Parkinson's Disease, amyotrophic lateral sclerosis, ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, drug induced toxic damage or hypoxia), or mitochondrial deregulation. In still further embodiments, the mitochondrial disease or disorder is a mitochondrial myopathy such as progressive external ophthalmoplegia, Kearns-Sayre syndrome, MELAS syndrome (mitochondrial encephalomyopathy, lactic acidosis, and stroke-like episodes), MERFF syndrome (myoclonic epilepsy and ragged red fibers), limb-girdle distribution weakness, or infantile myopathy (benign or severe and fatal).

In a further aspect, the invention provides a compound or pharmaceutical composition for use in therapy, wherein the compound is substantially isomerically pure β-D-nicotinamide riboside (2R (β) nicotinamide riboside) chloride crystal (3-carbamoyl-1-((2R,3R,4S,5R)-3,4-dihydroxy-5 (hydroxymethyl)tetrahydrofuran-2-yl)pyridin-1-ium (β-D-nicotinamide riboside (or 2R (β) nicotinamide riboside)) of greater than 90% chemical purity (w/w) containing <4000 ppm ethanol and <1000 ppm other solvents. In one embodiment, the compound or pharmaceutical composition is used in the treatment of a disease or disorder that would benefit from increased NAD levels (e.g., insulin resistance, a metabolic syndrome, diabetes, obesity, or a mitochondrial disease or disorder).

In another aspect, the compound or a pharmaceutical salt thereof is for use in the manufacture of a medicament for use in the treatment of a disease or disorder that would benefit from increased NAD levels (e.g., insulin resistance, a metabolic syndrome, diabetes, obesity, or a mitochondrial disease or disorder).

DETAILED DESCRIPTION OF THE INVENTION

Figure 1:
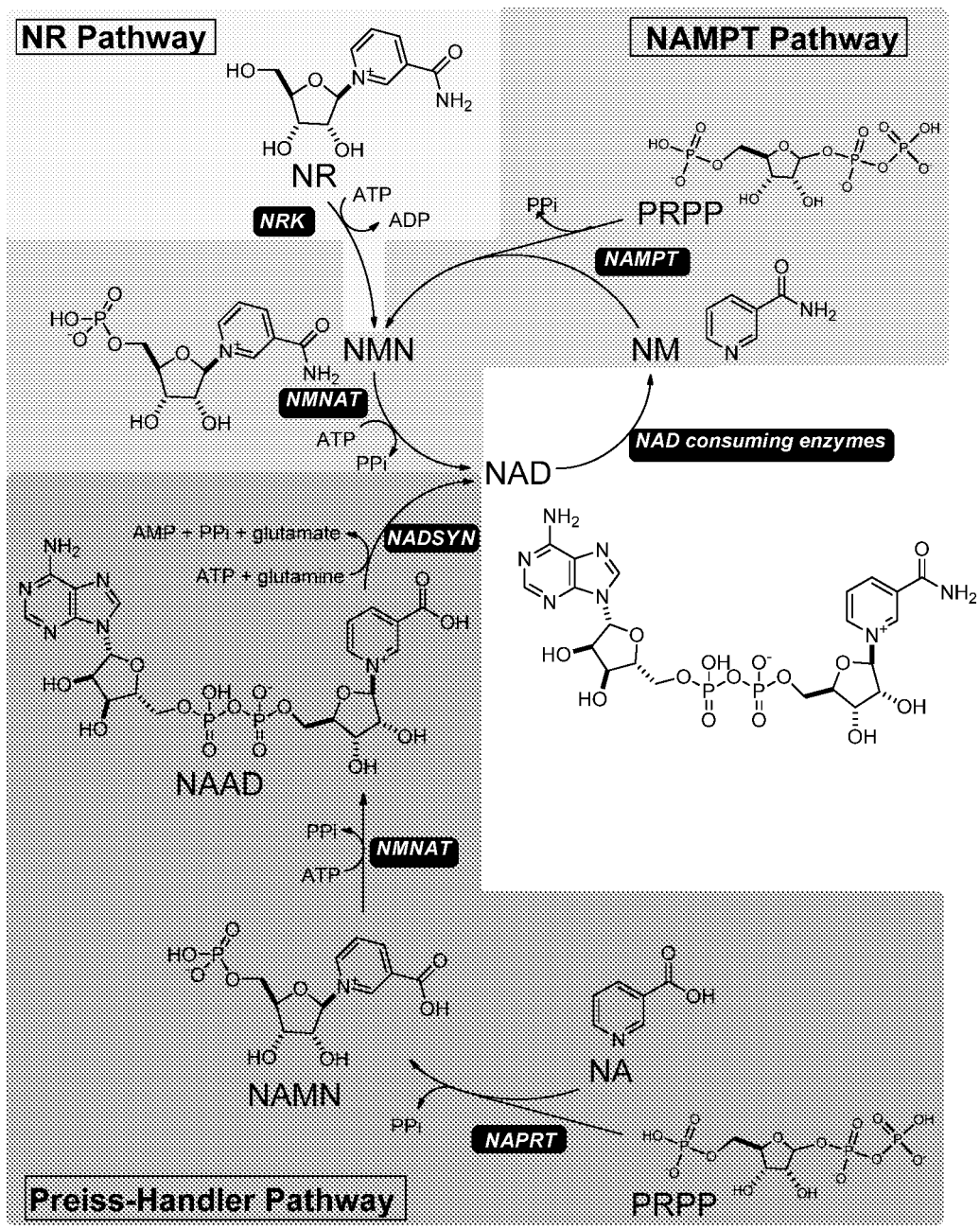
FIG. 1 depicts the NAD biosynthetic pathways affecting NAD metabolism including the Preiss-Handler pathway for niacin incorporation, the NR pathway utilizing exogenous NR, and the NAMPT pathway for nicotinic acid incorporation. The different biosynthetic pathways are shaded and labeled accordingly. Abbreviations of depicted compounds: ADP—adenosine diphosphate; ATP—adenosine triphosphate; NA—nicotinic acid; NAAD—nicotinic acid adenine dinucleotide; NAD—nicotinamide adenine dinucleotide; NAMN—nicotinic acid mononucleotide; NM—nicotinamide; NMN—nicotinamide mononucleotide NR—nicotinamide riboside; PRPP-5-phosphoribose-1-pyrophosphate; PPi—pyrophosphate. Enzyme Abbreviations: NAD consuming enzymes include ADPribosyl transferases, poly-ADPribosyl transferases, and sirtuins; NADSYN—NAD synthetase; NAPRT—nicotinic acid phosphoribosyl transferase; NAMPT—nicotinamide phosphoribosyltransferase; NMNAT—nicotinamide mononucleotide adenyl transferase.
Figure 2:
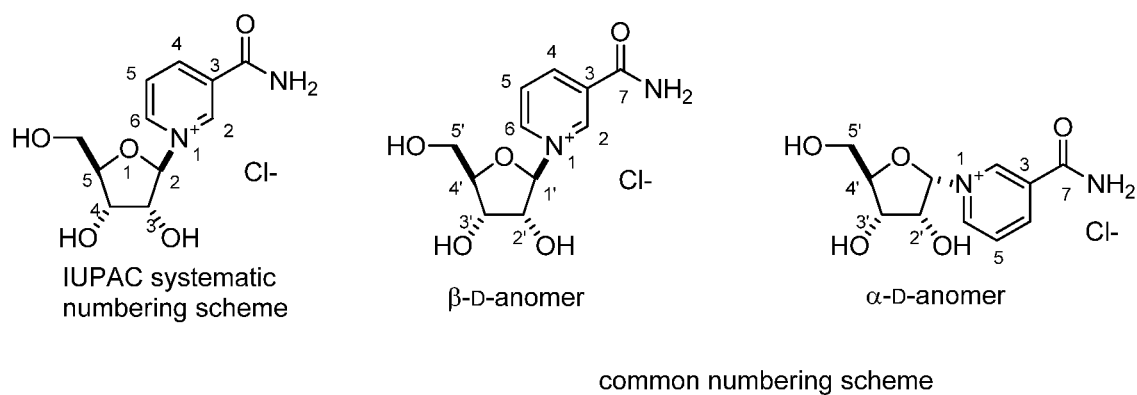
FIG. 2 depicts the chemical structure and numbering scheme of nicotinamide riboside chloride.

The present invention provides nicotinamide riboside chloride preparations and methods for using the same in the prophylaxis or treatment of a clinical condition in a mammal, such as a human, for which a NAD precursor is indicated, which comprises administration of a therapeutically effective amount of beta-D-nicotinamide riboside chloride. In particular, the present invention provides such a method for the prophylaxis or treatment of a disease or disorder that would benefit from increased NAD levels such as insulin resistance, a metabolic syndrome, diabetes, obesity, or a mitochondrial disease or disorder.

While it is possible for beta-D-nicotinamide riboside chloride to be administered alone, it may also be presented as a pharmaceutical formulation. Accordingly, the present invention further provides a pharmaceutical formulation comprising beta-D-nicotinamide riboside chloride and a pharmaceutically acceptable carrier or excipient, and optionally one or more other therapeutic ingredients.

Hereinafter, the term "active ingredient" means beta-D-nicotinamide riboside chloride, unless the context dictates otherwise.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Each capsule or cartridge may generally contain between 20 mg-10 g of the active ingredient optionally in combination with another therapeutically active ingredient. Alternatively, the compound of the invention may be presented without excipients. Packaging of the formulation may be suitable for unit dose or multi-dose delivery.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compound and pharmaceutical formulations according to the invention may be used in combination with or include one or more other therapeutic agents, for example selected from other NAD precursors, such nicotinamide mononucleotide (NMN), and/or niacin (nicotinic acid or vitamin B3). The invention thus provides, in a further aspect, a combination comprising beta-D-nicotinamide riboside together with one or more other therapeutically active agents, for example selected from an anti-inflammatory agent (for example a corticosteroid or an NSAID).

Pharmaceutical Compositions, Doses, and Dosage Regimens

When used in therapy, the nicotinamide riboside chloride salt of the invention is usually formulated in a pharmaceutical composition. Such compositions can be prepared using various procedures.

Thus, the present invention further provides a pharmaceutical composition for use in the treatment of a disease or disorder that would benefit from increased NAD levels such as insulin resistance, a metabolic syndrome, diabetes, obesity, or a mitochondrial disease or disorder, which comprises beta-D-nicotinamide riboside chloride and a pharmaceutically acceptable carrier.

A pharmaceutical composition of the invention, which may be prepared by admixture, for example at ambient temperature and/or atmospheric pressure, is usually adapted for oral, parenteral or rectal administration and, as such, may be in the form of a tablet, a capsule, an oral liquid preparation, a powder, granules, a lozenge, a reconstitutable powder, an injectable or infusible solution or suspension, or a suppository.

An orally administrable pharmaceutical composition, such as a tablet or capsule, is generally preferred.

A tablet or capsule for oral administration may be in unit dose form, and may contain one or more excipients, such as a binding agent (e.g. povidone, hydroxypropylmethylcellulose or starch), a filler (e.g. mannitol or lactose), microcrystalline cellulose, a lubricant e.g. tabletting lubricant (e.g. magnesium stearate, calcium stearate or stearic acid), a disintegrant e.g. tablet disintegrant, and/or a pharmaceutically acceptable wetting agent. A tablet may be coated, e.g. film-coated e.g. according to a tablet coating method. A capsule can be a hard or soft capsule, containing the compound or salt of the invention and the one or more excipients e.g. in powder or pellet form.

An oral liquid preparation may be in the form of, for example, an aqueous or oily suspension, a solution, an emulsion, a syrup or elixir, or may be in the form of a dry product for reconstitution with water or other suitable vehicle before use. Such liquid preparations may contain additive(s) such as suspending agents, emulsifying agents, non-aqueous vehicles (which may include edible oils), and/or preservatives, and/or, if desired, flavorings and/or colorants.

For parenteral administration, fluid unit dosage forms are typically prepared utilizing the compound of the invention or pharmaceutically acceptable salt thereof and a sterile vehicle. The compound or salt, e.g. depending on the vehicle and/or concentration used, can be either suspended or dissolved in the vehicle. In preparing solutions, the compound or salt can be dissolved for injection and filter sterilized before filling into a suitable vial or ampoule and sealing. Additive(s) such as a local anesthetic, preservative(s) and/or buffering agent(s) can be dissolved in the vehicle. To enhance the stability, the composition can be frozen after filling into the vial and the water removed under vacuum. Parenteral suspensions are typically prepared in substantially the same manner, except that the compound or salt is suspended in the vehicle instead of being dissolved, and sterilization typically is not accomplished by filtration. In one embodiment, the compound or salt is sterilized, e.g. by exposure to ethylene oxide, before suspension in a sterile vehicle. In one embodiment, a surfactant or wetting agent is included in the composition to facilitate uniform distribution of the compound or salt.

The pharmaceutical composition may contain from 0.1% to 99% by weight of the composition of the active material (i.e. beta-D-nicotinamide riboside chloride salt), in particular from 1 to 60% by weight or from 10 to 60% by weight of the composition of the active material. For example, this may vary depending on the route of administration and/or the composition's intended use(s).

The total amount of the pharmaceutically acceptable carrier in the pharmaceutical composition can for example vary depending on the pharmaceutical composition and/or its intended use and/or the route of administration. In one embodiment, the total amount of the pharmaceutically acceptable carrier in the pharmaceutical composition (e.g. or i.e. the total amount of the one or more excipients present therein, such as one or more of the excipient types mentioned herein), is in the range offrom 1% to 99.9% by weight of the composition, for example from 40% to 99% by weight such as from 40% to 90% by weight of the composition. Additionally or alternatively, in one embodiment, for a composition (e.g. composition for oral administration, e.g. tablet or capsule) in unit dose form, the total amount of the pharmaceutically acceptable carrier in the unit dose form pharmaceutical composition (e.g. or i.e. the total amount of the one or more excipients present therein) can be from 10 mg to 10,000 mg, e.g. from 10 mg to 2000 mg, from 20 mg to 1500 mg, or from 100 mg to about 1000 mg.

The dose, e.g. oral dose, of the beta-D-nicotinamide riboside chloride, e.g. used in the treatment or prophylaxis of the aforementioned disorders/diseases/conditions and/or comprised in a pharmaceutical composition, can for example vary in the usual way with the seriousness of the disorders, the weight of the sufferer, and/or other similar factors. In one embodiment, such a unit dose is for administration once a day, e.g. orally and/or to a mammal such as a human; alternatively such a unit dose may be for administration more than once a day, for example two or three times a day, e.g. orally and/or to a mammal such as a human. Such therapy may extend for a number of weeks, months or years.

Exemplary Uses

In certain aspects, the invention provides methods of treating or preventing a disease or disorder that would benefit from increased NAD levels, for example by increasing in vivo levels of NAD (e.g. intracellular NAD levels, levels of NAD in tissues or plasma, and/or overall NAD levels in an organism). Without wishing to be limited to a single mechanism, increased NAD levels serve to modulated the level and/or activity of one or more sirtuin proteins, e.g. by activating SIRT1 and or SIRT3.

In certain embodiments, the invention provides methods for using the nicotinamide riboside chloride preparations and pharmaceutical compositions of the invention to activate a sirtuin protein, e.g., increase the level and/or activity of a sirtuin protein. Increased sirtuin protein activity and/or increased sirtuin levels may be useful for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of a nicotinamide riboside chloride salt preparation or pharmaceutical preparation.

In certain embodiments, the nicotinamide riboside chloride preparations and pharmaceutical compositions described herein may be taken alone or in combination with other agents. In one embodiment, the nicotinamide riboside chloride preparations and pharmaceutical compositions may be administered to a subject in need thereof in conjunction with a sirtuin-modulating compound (e.g., an allosteric SIRT1 activators described in, e.g. WO 2007/019346, WO 2007/019344, WO 2008/156866, WO2008/156869, WO2010/071853, WO2009/134973, WO2010/003048, WO2010/037127, WO2010/037129, WO2013/059587, WO2013/059589, WO2013/059594, and WO 2011/059839). In another embodiment, the nicotinamide riboside chloride preparations and pharmaceutical composition may be administered with one or more of the following compounds: resveratrol, butein, fisetin, piceatannol, or quercetin. In an exemplary embodiment, the nicotinamide riboside chloride preparations and pharmaceutical composition may be administered in combination with nicotinic acid (i.e., niacin).

In another embodiment, the nicotinamide riboside chloride preparations or pharmaceutical composition of the invention may be administered with one or more of the following compounds that decrease the level and/or activity of a sirtuin protein: nicotinamide (NAM), suranim; EX527 (6-Chloro-2,3,4,9-tetrahydro-1H-carbazole-1-carboxamide); NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3', 4', 5'); (−)-epigallocatechin gallate (Hydroxy sites 5,7,3', 4', 5' and gallate ester on 3); cyanidin choloride (3,5,7,3', 4'-pentahydroxyflavylium chloride); delphinidin chloride (3,5,7,3', 4', 5'-hexahydroxyflavylium chloride); myricetin (cannabiscetin; 3,5,7,3', 4', 5'-hexahydroxyflavone); 3,7,3', 4', 5'-pentahydroxyflavone; gossypetin (3,5,7,8,3', 4'-hexahydroxyflavone), sirtinol; and splitomicin (see e.g., Howitz et al. (2003) Nature 425:191; Grozinger et al. (2001) J. Biol. Chem. 276:38837; Dedalov et al. (2001) PNAS 98:15113; and Hirao et al. (2003) J. Biol. Chem 278:52773). In yet another embodiment, the nicotinamide riboside chloride preparations or pharmaceutical composition of the invention may be administered with one or more therapeutic agents for the treatment or prevention of various diseases, including, for example, cancer, diabetes, neurodegenerative diseases, cardiovascular disease, blood clotting, inflammation, flushing, obesity, ageing, stress, etc. In various embodiments, combination therapies comprising the nicotinamide riboside chloride preparations or pharmaceutical composition of the invention may refer to (1) pharmaceutical compositions that comprise one or more of the nicotinamide riboside chloride preparations or pharmaceutical composition of the invention in combination with one or more therapeutic agents; and (2) co-administration of one or more of the nicotinamide riboside chloride preparations or pharmaceutical composition of the invention with one or more therapeutic agents wherein the nicotinamide riboside chloride preparations or pharmaceutical composition and the therapeutic agent have not been formulated in the same compositions. When using separate formulations, the nicotinamide riboside chloride preparations or pharmaceutical composition of the invention may be administered at the same, intermittent, staggered, prior to, subsequent to, or combinations of times thereof, with the administration of another therapeutic agent.

In certain embodiments, methods for reducing, preventing or treating diseases or disorders using of the nicotinamide riboside chloride preparations or pharmaceutical composition of the invention may also comprise increasing the protein level of a sirtuin, such as human SIRT1 or homologs thereof. Increasing protein levels can be achieved by introducing into a cell one or more copies of a nucleic acid that encodes a sirtuin. For example, the level of a sirtuin can be increased in a mammalian cell by introducing into the mammalian cell a nucleic acid encoding the sirtuin, e.g., increasing the level of SIRT1 by introducing a nucleic acid encoding the amino acid sequence set forth in GenBank Accession No. NP_036370. The nucleic acid may be under the control of a promoter that regulates the expression of the SIRT1 nucleic acid. Alternatively, the nucleic acid may be introduced into the cell at a location in the genome that is downstream of a promoter. Methods for increasing the level of a protein using these methods are well known in the art.

A nucleic acid that is introduced into a cell to increase the protein level of a sirtuin may encode a protein that is at least about 80%, 85%, 90%, 95%, 98%, or 99% identical to the sequence of a sirtuin, e.g., GenBank Accession No. NP_036370. For example, the nucleic acid encoding the protein may be at least about 80%, 85%, 90%, 95%, 98%, or 99% identical to GenBank Accession No. NM_012238. The nucleic acid may also be a nucleic acid that hybridizes, preferably under stringent hybridization conditions, to a nucleic acid encoding a wild-type sirtuin, e.g., GenBank Accession No. NM_012238. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having GenBank Accession No. NP_036370, preferably contains the core structure thereof. The core structure sometimes refers to amino acids 62-293 of GenBank Accession No. NP_036370, which are encoded by nucleotides 237 to 932 of GenBank Accession No. NM_012238, which encompasses the NAD binding as well as the substrate binding domains. The core domain of SIRT1 may also refer to about amino acids 261 to 447 of GenBank Accession No. NP_036370, which are encoded by nucleotides 834 to 1394 of GenBank Accession No. NM_012238; to about amino acids 242 to 493 of GenBank Accession No. NP_036370, which are encoded by nucleotides 777 to 1532 of GenBank Accession No. NM_012238; or to about amino acids 254 to 495 of GenBank Accession No. NP_036370, which are encoded by nucleotides 813 to 1538 of GenBank Accession No. NM_012238. Whether a protein retains a biological function, e.g., deacetylation capabilities, can be determined according to methods known in the art.

In certain embodiments, methods for reducing, preventing or treating diseases or disorders using the nicotinamide riboside chloride preparations or pharmaceutical composition of the invention may also comprise decreasing the protein level of a sirtuin, such as human SIRT1 or homologs thereof. Decreasing a sirtuin protein level can be achieved according to methods known in the art. For example, an siRNA, an antisense nucleic acid, or a ribozyme targeted to the sirtuin can be expressed in the cell. A dominant negative sirtuin mutant, e.g., a mutant that is not capable of deacetylating, may also be used. For example, mutant H363Y of SIRT1, described, e.g., in Luo et al. (2001) Cell 107:137 can be used. Alternatively, agents that inhibit transcription can be used.

Methods for modulating sirtuin protein levels also include methods for modulating the transcription of genes encoding sirtuins, methods for stabilizing/destabilizing the corresponding mRNAs, and other methods known in the art.

Aging/Stress

In one aspect of the invention, the disease or disorder that would benefit from increased NAD levels relates to aging and/or stress. Accordingly, in one embodiment the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with the nicotinamide riboside chloride preparations and pharmaceutical compositions of the invention.

For example, the methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with a sirtuin-modulating compound that increases the level and/or activity of a sirtuin protein to keep the cells, or progeny thereof, in culture for longer periods of time. Such cells can also be used for transplantation into a subject, e.g., after ex vivo modification.

In one embodiment, cells that are intended to be preserved for long periods of time may be treated with the nicotinamide riboside chloride preparations and pharmaceutical compositions of the invention that increases the in vivo levels of NAD (i.e, intracellular NAD levels). The cells may be in suspension (e.g., blood cells, serum, biological growth media, etc.) or in tissues or organs. For example, blood collected from an individual for purposes of transfusion may be treated with a sirtuin-modulating compound that increases the level and/or activity of a sirtuin protein to preserve the blood cells for longer periods of time. Additionally, blood to be used for forensic purposes may also be preserved using the nicotinamide riboside chloride preparations and pharmaceutical compositions of the invention. Other cells that may be treated to extend their lifespan or protect against apoptosis include cells for consumption, e.g., cells from non-human mammals (such as meat) or plant cells (such as vegetables).

The nicotinamide riboside chloride preparations and pharmaceutical compositions of the invention that increase the level of NAD, and/or the activity of a sirtuin protein may also be applied during developmental and growth phases in mammals, plants, insects or microorganisms, in order to, e.g., alter, retard or accelerate the developmental and/or growth process.

In another embodiment, the nicotinamide riboside chloride preparations and pharmaceutical compositions of the invention that increase the level of NAD and/or the activity of a sirtuin protein may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the using the nicotinamide riboside chloride preparations and pharmaceutical compositions of the invention prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with the nicotinamide riboside chloride preparations or pharmaceutical compositions of the invention, or may have a subset of cells/tissue treated locally with the nicotinamide riboside chloride preparations and pharmaceutical compositions of the invention that increase the level of NAD and/or activity of a sirtuin protein. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with the nicotinamide riboside chloride preparations and pharmaceutical compositions of the invention that increases the level of NAD and/or the activity of a sirtuin protein in vivo, e.g., to increase their lifespan or prevent apoptosis. For example, skin can be protected from aging (e.g., developing wrinkles, loss of elasticity, etc.) by treating skin or epithelial cells with the nicotinamide riboside chloride preparations and pharmaceutical compositions of the invention that increases the level of NAD and/or the activity of a sirtuin protein. In an exemplary embodiment, skin is contacted with a pharmaceutical or cosmetic composition comprising a nicotinamide riboside chloride preparation or pharmaceutical composition of the invention that increases the level of NAD and/or activity of a sirtuin protein. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, the nicotinamide riboside chloride preparations and pharmaceutical compositions of the invention that increase the level of NAD and/or activity of a sirtuin protein may be used for the treatment of wounds and/or burns to promote healing, including, for example, first-, second- or third-degree burns and/or thermal, chemical or electrical burns. The formulations may be administered topically, to the skin or mucosal tissue, as an ointment, lotion, cream, microemulsion, gel, solution or the like, as further described herein, within the context of a dosing regimen effective to bring about the desired result.

Topical formulations comprising one or more sirtuin-modulating compounds that increase the level and/or activity of a sirtuin protein may also be used as preventive, e.g., chemopreventive, compositions. When used in a chemopreventive method, susceptible skin is treated prior to any visible condition in a particular individual.

The nicotinamide riboside chloride preparations and pharmaceutical compositions of the invention may be delivered locally or systemically to a subject. In one embodiment, the nicotinamide riboside chloride preparations and pharmaceutical compositions of the invention is delivered locally to a tissue or organ of a subject by injection, topical formulation, etc.

In another embodiment, a nicotinamide riboside chloride preparation or pharmaceutical compositions of the invention that increases the level of NAD and/or the activity of a sirtuin protein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, the nicotinamide riboside chloride preparations and pharmaceutical compositions of the invention that increases the level of NAD and/or activity of a sirtuin protein may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

The nicotinamide riboside chloride preparations and pharmaceutical compositions of the invention that increase the level of NAD and/or activity of a sirtuin protein can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

The nicotinamide riboside chloride preparations and pharmaceutical compositions of the invention that increase the level of NAD and/or activity of a sirtuin protein can also be administered to a subject suffering from an acute disease, e.g., damage to an organ or tissue, e.g., a subject suffering from stroke or myocardial infarction or a subject suffering from a spinal cord injury. The nicotinamide riboside chloride preparations and pharmaceutical compositions of the invention that increase the level of NAD and/or activity of a sirtuin protein may also be used to repair an alcoholic's liver.

Cardiovascular Disease

In another embodiment, the invention provides a method for treating and/or preventing a cardiovascular disease by administering to a subject in need thereof a nicotinamide riboside chloride preparations or pharmaceutical compositions of the invention that increases the level of NAD and/or the activity of a sirtuin protein.

Cardiovascular diseases that can be treated or prevented using the nicotinamide riboside chloride preparations and pharmaceutical compositions of the invention that increase the level of NAD and/or the activity of a sirtuin protein include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The nicotinamide riboside chloride preparations and pharmaceutical compositions of the invention that increase the level of NAD and/or activity of a sirtuin protein may also be used for increasing HDL levels in plasma of an individual.

Yet other disorders that may be treated with sirtuin-modulating compounds that increase the level of NAD and/or the activity of a sirtuin protein include restenosis, e.g., following coronary intervention, and disorders relating to an abnormal level of high density and low density cholesterol.

In one embodiment, a nicotinamide riboside chloride preparation or pharmaceutical composition of the invention that increases the level of NAD and/or the activity of a sirtuin protein may be administered as part of a combination therapeutic with another cardiovascular agent including, for example, an anti-arrhythmic agent, an antihypertensive agent, a calcium channel blocker, a cardioplegic solution, a cardiotonic agent, a fibrinolytic agent, a sclerosing solution, a vasoconstrictor agent, a vasodilator agent, a nitric oxide donor, a potassium channel blocker, a sodium channel blocker, statins, or a naturiuretic agent.

In one embodiment, a nicotinamide riboside chloride preparations or pharmaceutical composition of the invention that increases the level and/or activity of NAD and/or the activity of a sirtuin protein may be administered as part of a combination therapeutic with an anti-arrhythmia agent. Anti-arrhythmia agents are often organized into four main groups according to their mechanism of action: type I, sodium channel blockade; type II, beta-adrenergic blockade; type III, repolarization prolongation; and type IV, calcium channel blockade. Type I anti-arrhythmic agents include lidocaine, moricizine, mexiletine, tocainide, procainamide, encainide, flecanide, tocainide, phenytoin, propafenone, quinidine, disopyramide, and flecainide. Type II anti-arrhythmic agents include propranolol and esmolol. Type III includes agents that act by prolonging the duration of the action potential, such as amiodarone, artilide, bretylium, clofilium, isobutilide, sotalol, azimilide, dofetilide, dronedarone, ersentilide, ibutilide, tedisamil, and trecetilide. Type IV anti-arrhythmic agents include verapamil, diltaizem, digitalis, adenosine, nickel chloride, and magnesium ions.

In another embodiment, a nicotinamide riboside chloride preparation or pharmaceutical composition of the invention that increases the level of NAD and/or the activity of a sirtuin protein may be administered as part of a combination therapeutic with another cardiovascular agent. Examples of cardiovascular agents include vasodilators, for example, hydralazine; angiotensin converting enzyme inhibitors, for example, captopril; anti-anginal agents, for example, isosorbide nitrate, glyceryl trinitrate and pentaerythritol tetranitrate; anti-arrhythmic agents, for example, quinidine, procainaltide and lignocaine; cardioglycosides, for example, digoxin and digitoxin; calcium antagonists, for example, verapamil and nifedipine; diuretics, such as thiazides and related compounds, for example, bendrofluazide, chlorothiazide, chlorothalidone, hydrochlorothiazide and other diuretics, for example, fursemide and triamterene, and sedatives, for example, nitrazepam, flurazepam and diazepam.

Other exemplary cardiovascular agents include, for example, a cyclooxygenase inhibitor such as aspirin or indomethacin, a platelet aggregation inhibitor such as clopidogrel, ticlopidene or aspirin, fibrinogen antagonists or a diuretic such as chlorothiazide, hydrochlorothiazide, flumethiazide, hydroflumethiazide, bendroflumethiazide, methylchlorthiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, angiotensin II antagonists such as losartan, irbesartan or valsartan, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or animal salivary gland plasminogen activators, calcium channel blocking agents such as verapamil, nifedipine or diltiazem, thromboxane receptor antagonists such as ifetroban, prostacyclin mimetics, or phosphodiesterase inhibitors. Such combination products if formulated as a fixed dose employ the compounds of this invention within the dose range described above and the other pharmaceutically active agent within its approved dose range.

Yet other exemplary cardiovascular agents include, for example, vasodilators, e.g., bencyclane, cinnarizine, citicoline, cyclandelate, cyclonicate, ebumamonine, phenoxezyl, flunarizine, ibudilast, ifenprodil, lomerizine, naphlole, nikamate, nosergoline, nimodipine, papaverine, pentifylline, nofedoline, vincamin, vinpocetine, vichizyl, pentoxifylline, prostacyclin derivatives (such as prostaglandin E1 and prostaglandin I2), an endothelin receptor blocking drug (such as bosentan), diltiazem, nicorandil, and nitroglycerin. Examples of the cerebral protecting drug include radical scavengers (such as edaravone, vitamin E, and vitamin C), glutamate antagonists, AMPA antagonists, kainate antagonists, NMDA antagonists, GABA agonists, growth factors, opioid antagonists, phosphatidylcholine precursors, serotonin agonists, Na+/Ca2+ channel inhibitory drugs, and K+ channel opening drugs. Examples of the brain metabolic stimulants include amantadine, tiapride, and gamma-aminobutyric acid. Examples of the anticoagulant include heparins (such as heparin sodium, heparin potassium, dalteparin sodium, dalteparin calcium, heparin calcium, parnaparin sodium, reviparin sodium, and danaparoid sodium), warfarin, enoxaparin, argatroban, batroxobin, and sodium citrate. Examples of the antiplatelet drug include ticlopidine hydrochloride, dipyridamole, cilostazol, ethyl icosapentate, sarpogrelate hydrochloride, dilazep hydrochloride, trapidil, a nonsteroidal antiinflammatory agent (such as aspirin), beraprostsodium, iloprost, and indobufene. Examples of the thrombolytic drug include urokinase, tissue-type plasminogen activators (such as alteplase, tisokinase, nateplase, pamiteplase, monteplase, and rateplase), and nasaruplase. Examples of the antihypertensive drug include angiotensin converting enzyme inhibitors (such as captopril, alacepril, lisinopril, imidapril, quinapril, temocapril, delapril, benazepril, cilazapril, trandolapril, enalapril, ceranopril, fosinopril, imadapril, mobertpril, perindopril, ramipril, spirapril, and randolapril), angiotensin II antagonists (such as losartan, candesartan, valsartan, eprosartan, and irbesartan), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendilin, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline), beta-adrenaline receptor blocking drugs (propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nebivolol, oxprenolol, practol, pronetalol, sotalol, sufinalol, talindolol, tertalol, toliprolol, xybenolol, and esmolol), alpha-receptor blocking drugs (such as amosulalol, prazosin, terazosin, doxazosin, bunazosin, urapidil, phentolamine, arotinolol, dapiprazole, fenspiride, indoramin, labetalol, naftopidil, nicergoline, tamsulosin, tolazoline, trimazosin, and yohimbine), sympathetic nerve inhibitors (such as clonidine, guanfacine, guanabenz, methyldopa, and reserpine), hydralazine, todralazine, budralazine, and cadralazine. Examples of the antianginal drug include nitrate drugs (such as amyl nitrite, nitroglycerin, and isosorbide), beta-adrenaline receptor blocking drugs (such as propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nebivolol, oxprenolol, practol, pronetalol, sotalol, sufinalol, talindolol, tertalol, toliprolol, andxybenolol), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendiline, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline) trimetazidine, dipyridamole, etafenone, dilazep, trapidil, nicorandil, enoxaparin, and aspirin. Examples of the diuretic include thiazide diuretics (such as hydrochlorothiazide, methyclothiazide, trichlormethiazide, benzylhydrochlorothiazide, and penflutizide), loop diuretics (such as furosemide, etacrynic acid, bumetanide, piretanide, azosemide, and torasemide), K+ sparing diuretics (spironolactone, triamterene, andpotassiumcanrenoate), osmotic diuretics (such as isosorbide, D-mannitol, and glycerin), nonthiazide diuretics (such as meticrane, tripamide, chlorthalidone, and mefruside), and acetazolamide. Examples of the cardiotonic include digitalis formulations (such as digitoxin, digoxin, methyldigoxin, deslanoside, vesnarinone, lanatoside C, and proscillaridin), xanthine formulations (such as aminophylline, choline theophylline, diprophylline, and proxyphylline), catecholamine formulations (such as dopamine, dobutamine, and docarpamine), PDE III inhibitors (such as amrinone, olprinone, and milrinone), denopamine, ubidecarenone, pimobendan, levosimendan, aminoethylsulfonic acid, vesnarinone, carperitide, and colforsin daropate. Examples of the antiarrhythmic drug include ajmaline, pirmenol, procainamide, cibenzoline, disopyramide, quinidine, aprindine, mexiletine, lidocaine, phenyloin, pilsicainide, propafenone, flecainide, atenolol, acebutolol, sotalol, propranolol, metoprolol, pindolol, amiodarone, nifekalant, diltiazem, bepridil, and verapamil. Examples of the antihyperlipidemic drug include atorvastatin, simvastatin, pravastatin sodium, fluvastatin sodium, clinofibrate, clofibrate, simfibrate, fenofibrate, bezafibrate, colestimide, and colestyramine. Examples of the immunosuppressant include azathioprine, mizoribine, cyclosporine, tacrolimus, gusperimus, and methotrexate.

Cell Death/Cancer

The nicotinamide riboside chloride preparations and pharmaceutical compositions of the invention that increase the level of NAD and/or activity of a sirtuin protein may be administered to subjects who have recently received or are likely to receive a dose of radiation or toxin. In one embodiment, the dose of radiation or toxin is received as part of a work-related or medical procedure, e.g., working in a nuclear power plant, flying an airplane, an X-ray, CAT scan, or the administration of a radioactive dye for medical imaging; in such an embodiment, the compound is administered as a prophylactic measure. In another embodiment, the radiation or toxin exposure is received unintentionally, e.g., as a result of an industrial accident, habitation in a location of natural radiation, terrorist act, or act of war involving radioactive or toxic material. In such a case, the nicotinamide riboside chloride preparation or pharmaceutical composition of the invention is preferably administered as soon as possible after the exposure to inhibit apoptosis and the subsequent development of acute radiation syndrome.

The nicotinamide riboside chloride preparations and pharmaceutical compositions of the invention may also be used for treating and/or preventing cancer. In certain embodiments, the nicotinamide riboside chloride preparations and pharmaceutical compositions of the invention that increase the level of NAD and/or activity of a sirtuin protein may be used for treating and/or preventing cancer. Calorie restriction has been linked to a reduction in the incidence of age-related disorders including cancer (see e.g., Bordone and Guarente, Nat. Rev. Mol. Cell Biol. (2005 epub); Guarente and Picard, Cell 120: 473-82 (2005); Berrigan, et al., Carcinogenesis 23: 817-822 (2002); and Heilbronn and Ravussin, Am. J. Clin. Nutr. 78: 361-369 (2003)). Additionally, the Sir2 protein from yeast has been shown to be required for lifespan extension by glucose restriction (see e.g., Lin et al., Science 289: 2126-2128 (2000); Anderson et al., Nature 423: 181-185 (2003)), a yeast model for calorie restriction. Accordingly, an increase in the level of NAD and/or activity of a sirtuin protein may be useful for treating and/or preventing the incidence of age-related disorders, such as, for example, cancer.

In other embodiments, the nicotinamide riboside chloride preparations and pharmaceutical compositions of the invention may be used in conjunction with sirtuin-modulating compounds that decrease the level and/or activity of a sirtuin protein for the purpose of treating or preventing cancer. For example, inhibitory compounds may be used to stimulate acetylation of substrates such as p53 and thereby increase apoptosis, as well as to reduce the lifespan of cells and organisms, render them more sensitive to stress, and/or increase the radiosensitivity and/or chemosensitivity of a cell or organism. Thus, inhibitory compounds may be used, e.g., for treating cancer. Exemplary cancers that may be treated using a sirtuin-modulating compound are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth can also be treated, e.g., warts. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of sirtuin-modulating compound. Alternatively, cells can be obtained from a subject, treated ex vivo to remove certain undesirable cells, e.g., cancer cells, and administered back to the same or a different subject.

Furthermore, chemotherapeutic agents may be coadministered with the nicotinamide riboside chloride preparations and pharmaceutical compositions. Chemotherapeutic agents described herein as having anti-cancer activity (e.g., compounds that induce apoptosis, compounds that reduce lifespan or compounds that render cells sensitive to stress) include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; chromatin disruptors.

These chemotherapeutic agents may be used by themselves or with a a nicotinamide riboside preparation described herein as inducing cell death or reducing lifespan or increasing sensitivity to stress and/or in combination with other chemotherapeutics agents. Many combinatorial therapies have been developed, including but not limited to those listed in Table 1.

TABLE 1

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/ Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |

TABLE 1-continued

Exemplary combinatorial therapies for the treatment of cancer.

| Name | Therapeutic agents |
|---|---|
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP (Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |

TABLE 1-continued

Exemplary combinatorial therapies for the treatment of cancer.

| Name | Therapeutic agents |
| --- | --- |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In addition to conventional chemotherapeutics, the nicotinamide riboside chloride preparations and pharmaceutical compositions described herein as capable of inducing cell death or reducing lifespan can also be used with antisense RNA, RNAi or other polynucleotides to inhibit the expression of the cellular components that contribute to unwanted cellular proliferation that are targets of conventional chemotherapy. Such targets are, merely to illustrate, growth factors, growth factor receptors, cell cycle regulatory proteins, transcription factors, or signal transduction kinases.

Combination therapies comprising the nicotinamide riboside chloride preparations and pharmaceutical compositions of the invention and a conventional chemotherapeutic agent may be advantageous over combination therapies known in the art because the combination allows the conventional chemotherapeutic agent to exert greater effect at lower dosage. In a preferred embodiment, the effective dose (ED50) for a chemotherapeutic agent, or combination of conventional chemotherapeutic agents, when used in combination with a nicotinamide riboside chloride preparation is at least 2 fold less than the ED50 for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with the nicotinamide riboside chloride preparations and pharmaceutical compositions of the invention can be at least 2 fold greater than the TI for conventional chemotherapeutic regimen alone, and even more preferably at 5 fold, 10 fold or even 25 fold greater.

Neuronal Diseases/Disorders

In certain aspects, the nicotinamide riboside chloride preparations and pharmaceutical compositions of the invention that increase the level of NAD and/or the activity of a sirtuin protein can be used to treat patients suffering from neurodegenerative diseases, and traumatic or mechanical injury to the central nervous system (CNS) or peripheral nervous system (PNS). Neurodegenerative disease typically involves reductions in the mass and volume of the human brain, which may be due to the atrophy and/or death of brain cells, which are far more profound than those in a healthy person that are attributable to aging. Neurodegenerative diseases evolve gradually, after a long period of normal brain function, due to progressive degeneration (e.g., nerve cell dysfunction and death) of specific brain regions. The actual onset of brain degeneration may precede clinical expression by many years. Examples of neurodegenerative diseases include, but are not limited to, Alzheimer's disease (AD), Parkinson's disease (PD), Huntington disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. Nicotinamide riboside chloride preparations and pharmaceutical compositions of the invention that increase the level of NAD and/or activity of a sirtuin protein can be used to treat these disorders and others as described below.

AD is a chronic, incurable, and unstoppable CNS disorder that occurs gradually, resulting in memory loss, unusual behavior, personality changes, and a decline in thinking abilities. These losses are related to the death of specific types of brain cells and the breakdown of connections between them. AD has been described as childhood development in reverse. In most people with AD, symptoms appear after the age 60. The earliest symptoms include loss of recent memory, faulty judgment, and changes in personality. Later in the disease, those with AD may forget how to do simple tasks like washing their hands. Eventually people with AD lose all reasoning abilities and become dependent on other people for their everyday care. Finally, the disease becomes so debilitating that patients are bedridden and typically develop coexisting illnesses.

PD is a chronic, incurable, and unstoppable CNS disorder that occurs gradually and results in uncontrolled body movements, rigidity, tremor, and gait difficulties. These motor system problems are related to the death of brain cells in an area of the brain that produces dopamine, a chemical that helps control muscle activity. In most people with PD, symptoms appear after age 50. The initial symptoms of PD are a pronounced tremor affecting the extremities, notably in the hands or lips. Subsequent characteristic symptoms of PD are stiffness or slowness of movement, a shuffling walk, stooped posture, and impaired balance. There are wide ranging secondary symptoms such as memory loss, dementia, depression, emotional changes, swallowing difficulties, abnormal speech, sexual dysfunction, and bladder and bowel problems. These symptoms will begin to interfere with routine activities, such as holding a fork or reading a newspaper. Finally, people with PD become so profoundly disabled that they are bedridden.

ALS (motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles. Most people who get ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheelchair or become unable to function out of bed.

The causes of these neurological diseases have remained largely unknown. They are conventionally defined as distinct diseases, yet clearly show extraordinary similarities in basic processes and commonly demonstrate overlapping symptoms far greater than would be expected by chance alone. Current disease definitions fail to properly deal with the issue of overlap and a new classification of the neurodegenerative disorders has been called for.

HD is another neurodegenerative disease resulting from genetically programmed degeneration of neurons in certain areas of the brain. This degeneration causes uncontrolled movements, loss of intellectual faculties, and emotional disturbance. HD is a familial disease, passed from parent to child through a dominant mutation in the wild-type gene. Some early symptoms of HD are mood swings, depression, irritability or trouble driving, learning new things, remembering a fact, or making a decision. As the disease progresses, concentration on intellectual tasks becomes increasingly difficult and the patient may have difficulty feeding himself or herself and swallowing.

Tay-Sachs disease and Sandhoff disease are glycolipid storage diseases caused by the lack of lysosomal β-hexosaminidase (Gravel et al., in The Metabolic Basis of Inherited Disease, eds. Scriver et al., McGraw-Hill, N.Y., pp. 2839-2879, 1995). In both disorders, GM2 ganglioside and related glycolipidssubstrates for β-hexosaminidase accumulate in the nervous system and trigger acute neurodegeneration. In the most severe forms, the onset of symptoms begins in early infancy. A precipitous neurodegenerative course then ensues, with affected infants exhibiting motor dysfunction, seizure, visual loss, and deafness. Death usually occurs by 2-5 years of age. Neuronal loss through an apoptotic mechanism has been demonstrated (Huang et al., Hum. Mol. Genet. 6: 1879-1885, 1997).

It is well-known that apoptosis plays a role in AIDS pathogenesis in the immune system. However, HIV-1 also induces neurological disease. Shi et al. (J. Clin. Invest. 98: 1979-1990, 1996) examined apoptosis induced by HIV-1 infection of the CNS in an in vitro model and in brain tissue from AIDS patients, and found that HIV-1 infection of primary brain cultures induced apoptosis in neurons and astrocytes in vitro. Apoptosis of neurons and astrocytes was also detected in brain tissue from 10/11 AIDS patients, including 5/5 patients with HIV-1 dementia and 4/5 nondemented patients.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. Sirtuin-modulating compounds that increase the level and/or activity of a sirtuin protein may be useful for treating or preventing neuronal loss due to these prior diseases.

In another embodiment, a nicotinamide riboside chloride preparations or pharmaceutical compositions of the invention that increases the level of NAD and/or activity of a sirtuin protein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. The most common cause of distal axonopathy is diabetes, and the most common distal axonopathy is diabetic neuropathy. The most distal portions of axons are usually the first to degenerate, and axonal atrophy advances slowly towards the nerve's cell body. If the noxious stimulus is removed, regeneration is possible, though prognosis decreases depending on the duration and severity of the stimulus. Those with distal axonopathies usually present with symmetrical stocking-glove sensorimotor disturbances. Deep tendon reflexes and autonomic nervous system (ANS) functions are also lost or diminished in affected areas.

Diabetic neuropathies are neuropathic disorders that are associated with diabetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy. Clinical manifestations of diabetic neuropathy include, for example, sensorimotor polyneuropathy such as numbness, sensory loss, dysesthesia and nighttime pain; autonomic neuropathy such as delayed gastric emptying or gastroparesis; and cranial neuropathy such as oculomotor (3rd) neuropathies or Mononeuropathies of the thoracic or lumbar spinal nerves.

Peripheral neuropathy is the medical term for damage to nerves of the peripheral nervous system, which may be caused either by diseases of the nerve or from the side-effects of systemic illness. Peripheral neuropathies vary in their presentation and origin, and may affect the nerve or the neuromuscular junction. Major causes of peripheral neuropathy include seizures, nutritional deficiencies, and HIV, though diabetes is the most likely cause.

Mechanical pressure from staying in one position for too long, a tumor, intraneural hemorrhage, exposing the body to extreme conditions such as radiation, cold temperatures, or toxic substances can also cause peripheral neuropathy.

In an exemplary embodiment, a nicotinamide riboside chloride preparation or pharmaceutical compositions of the invention that increases the level of NAD and/or activity of a sirtuin protein may be used to treat or prevent multiple sclerosis (MS), including relapsing MS and monosymptomatic MS, and other demyelinating conditions, such as, for example, chromic inflammatory demyelinating polyneuropathy (CIDP), or symptoms associated therewith.

MS is a chronic, often disabling disease of the central nervous system. Various and converging lines of evidence point to the possibility that the disease is caused by a disturbance in the immune function, although the cause of this disturbance has not been established. This disturbance permits cells of the immune system to "attack" myelin, the fat containing insulating sheath that surrounds the nerve axons located in the central nervous system ("CNS"). When myelin is damaged, electrical pulses cannot travel quickly or normally along nerve fiber pathways in the brain and spinal cord. This results in disruption of normal electrical conductivity within the axons, fatigue and disturbances of vision, strength, coordination, balance, sensation, and bladder and bowel function.

As such, MS is now a common and well-known neurological disorder that is characterized by episodic patches of inflammation and demyelination which can occur anywhere in the CNS. However, almost always without any involvement of the peripheral nerves associated therewith. Demyelination produces a situation analogous to that resulting from cracks or tears in an insulator surrounding an electrical cord. That is, when the insulating sheath is disrupted, the circuit is "short circuited" and the electrical apparatus associated therewith will function intermittently or nor at all. Such loss of myelin surrounding nerve fibers results in short circuits in nerves traversing the brain and the spinal cord that thereby result in symptoms of MS. It is further found that such demyelination occurs in patches, as opposed to along the entire CNS. In addition, such demyelination may be intermittent. Therefore, such occurrences are disseminated in both time and space.

It is believed that the pathogenesis involves a local disruption of the blood brain barrier which causes a localized immune and inflammatory response, with consequent damage to myelin and hence to neurons.

Clinically, MS exists in both sexes and can occur at any age. However, its most common presentation is in the relatively young adult, often with a single focal lesion such as a damage of the optic nerve, an area of anesthesia (loss of sensation), or paraesthesia (localize loss of feeling), or muscular weakness. In addition, vertigo, double vision, localized pain, incontinence, and pain in the arms and legs may occur upon flexation of the neck, as well as a large variety of less common symptoms.

An initial attack of MS is often transient, and it may be weeks, months, or years before a further attack occurs. Some individuals may enjoy a stable, relatively event free condition for a great number of years, while other less fortunate ones may experience a continual downhill course ending in complete paralysis. There is, most commonly, a series of remission and relapses, in which each relapse leaves a patient somewhat worse than before. Relapses may be triggered by stressful events, viral infections or toxins. Therein, elevated body temperature, i.e., a fever, will make the condition worse, or as a reduction of temperature by, for example, a cold bath, may make the condition better.

In yet another embodiment, a nicotinamide riboside chloride preparation or pharmaceutical composition of the invention that increases the level of NAD and/or activity of a sirtuin protein may be used to treat trauma to the nerves, including, trauma due to disease, injury (including surgical intervention), or environmental trauma (e.g., neurotoxins, alcoholism, etc.).

Nicotinamide riboside chloride preparations and pharmaceutical compositions of the invention that increase the level of NAD and/or activity of a sirtuin protein may also be useful to prevent, treat, and alleviate symptoms of various PNS disorders, such as the ones described below. The PNS is composed of the nerves that lead to or branch off from the CNS. The peripheral nerves handle a diverse array of functions in the body, including sensory, motor, and autonomic functions. When an individual has a peripheral neuropathy, nerves of the PNS have been damaged. Nerve damage can arise from a number of causes, such as disease, physical injury, poisoning, or malnutrition. These agents may affect either afferent or efferent nerves. Depending on the cause of damage, the nerve cell axon, its protective myelin sheath, or both may be injured or destroyed.

The term "peripheral neuropathy" encompasses a wide range of disorders in which the nerves outside of the brain and spinal cord—peripheral nerves—have been damaged.

Peripheral neuropathy may also be referred to as peripheral neuritis, or if many nerves are involved, the terms polyneuropathy or polyneuritis may be used.

Peripheral neuropathy is a widespread disorder, and there are many underlying causes. Some of these causes are common, such as diabetes, and others are extremely rare, such as acrylamide poisoning and certain inherited disorders. The most common worldwide cause of peripheral neuropathy is leprosy. Leprosy is caused by the bacterium Mycobacterium leprae, which attacks the peripheral nerves of affected people.

Leprosy is extremely rare in the United States, where diabetes is the most commonly known cause of peripheral neuropathy. It has been estimated that more than 17 million people in the United States and Europe have diabetes-related polyneuropathy. Many neuropathies are idiopathic; no known cause can be found. The most common of the inherited peripheral neuropathies in the United States is Charcot-Marie-Tooth disease, which affects approximately 125,000 persons.

Another of the better known peripheral neuropathies is Guillain-Barré syndrome, which arises from complications associated with viral illnesses, such as cytomegalovirus, Epstein-Barr virus, and human immunodeficiency virus (HIV), or bacterial infection, including Campylobacter jejuni and Lyme disease. The worldwide incidence rate is approximately 1.7 cases per 100,000 people annually. Other well-known causes of peripheral neuropathies include chronic alcoholism, infection of the varicella-zoster virus, botulism, and poliomyelitis. Peripheral neuropathy may develop as a primary symptom, or it may be due to another disease. For example, peripheral neuropathy is only one symptom of diseases such as amyloid neuropathy, certain cancers, or inherited neurologic disorders. Such diseases may affect the PNS and the CNS, as well as other body tissues.

Other PNS diseases treatable with compounds that increase the level activity of a sirtuin protein include: Brachial Plexus Neuropathies (diseases of the cervical and first thoracic roots, nerve trunks, cords, and peripheral nerve components of the brachial plexus. Clinical manifestations include regional pain, paresthesia; muscle weakness, and decreased sensation in the upper extremity. These disorders may be associated with trauma, including birth injuries; thoracic outlet syndrome; neoplasms, neuritis, radiotherapy; and other conditions. See Adams et al., Principles of Neurology, 6th ed, pp 1351-2); Diabetic Neuropathies (peripheral, autonomic, and cranial nerve disorders that are associated with diabetes mellitus). These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy (see Adams et al., Principles of Neurology, 6th ed, p 1325); mononeuropathies (disease or trauma involving a single peripheral nerve in isolation, or out of proportion to evidence of diffuse peripheral nerve dysfunction). Mononeuropathy multiplex refers to a condition characterized by multiple isolated nerve injuries. Mononeuropathies may result from a wide variety of causes, including ischemia; traumatic injury; compression; connective tissue diseases; cumulative trauma disorders; and other conditions; Neuralgia (intense or aching pain that occurs along the course or distribution of a peripheral or cranial nerve); Peripheral Nervous System Neoplasms (neoplasms which arise from peripheral nerve tissue). This includes neurofibromas; Schwannomas; granular cell tumors; and malignant peripheral nerve sheath tumors. See DeVita Jr et al., Cancer: Principles and Practice of Oncology, 5th ed, pp 1750-1); and Nerve Compression Syndromes (mechanical compression of nerves or nerve roots from internal or external causes). These may result in a conduction block to nerve impulses, due to, for example, myelin sheath dysfunction, or axonal loss. The nerve and nerve sheath injuries may be caused by ischemia; inflammation; or a direct mechanical effect; Neuritis (a general term indicating inflammation of a peripheral or cranial nerve). Clinical manifestation may include pain; paresthesias; paresis; or hyperthesia; Polyneuropathies (diseases of multiple peripheral nerves). The various forms are categorized by the type of nerve affected (e.g., sensory, motor, or autonomic), by the distribution of nerve injury (e.g., distal vs. proximal), by nerve component primarily affected (e.g., demyelinating vs. axonal), by etiology, or by pattern of inheritance.

In one embodiment, a combination drug regimen may include drugs or compounds for the treatment or prevention of neurodegenerative disorders or secondary conditions associated with these conditions. Thus, a combination drug regimen may include one or more nicotinamide riboside chloride preparation or pharmaceutical composition of the invention that increase the level of NAD and/or activity of a sirtuin protein and one or more anti-neurodegeneration agents. For example, one or more nicotinamide riboside chloride preparation or pharmaceutical composition of the invention can be combined with an effective amount of one or more of: L-DOPA; a dopamine agonist; an adenosine A2A receptor antagonists; a COMT inhibitor; a MAO inhibitor; an NOS inhibitor; a sodium channel antagonist; a selective N-methyl D-aspartate (NMDA) receptor antagonists; an AMPA/kainate receptor antagonist; a calcium channel antagonist; a GABA-A receptor agonist; an acetylcholine esterase inhibitor; a matrix metalloprotease inhibitor; an inhibitor of p38 MAP kinase or c-jun-N-terminal kinases; TPA; NDA antagonists; beta-interferons; growth factors; glutamate inhibitors; and/or as part of a cell therapy.

Exemplary N-NOS inhibitors include 4-(6-amino-pyridin-2-yl)-3-methoxyphenol 6-[4-(2-dimethylamino-ethoxy)-2-methoxy-phenyl]-pyridin-2-yl-amine, 6-[4-(2-dimethylamino-ethoxy)-2,3-dimet-hyl-phenyl]-pyridin-2-yl-amine, 6-[4-(2-pyrrolidinyl-ethoxy)-2,3-dimethyl-p-henyl]-pyridin-2-yl-amine, 6-[4-(4-(n-methyl)piperidinyloxy)-2,3-dimethyl-p-henyl]-pyridin-2-yl-amine, 6-[4-(2-dimethylamino-ethoxy)-3-methoxy-phenyl]-pyridin-2-yl-amine, 6-[4-(2-pyrrolidinyl-ethoxy)-3-methoxy-phenyl]-pyridin-2-yl-amine, 6-{4-[2-(6,7-dimethoxy-3,4-dihydro-1h-isoquinolin-2-yl)-ethoxy]-3-methoxy-phenyl}-pyridin-2-yl-amine, 6-{3-methoxy-4-[2-(4-phenethyl-piper-azin-1-yl)-ethoxy]-phenyl}-pyridin-2-yl-amine, 6-{3-methoxy-4-[2-(4-methyl-piperazin-1-yl)-ethoxy]-phenyl}-pyridin-2-yl-amine, 6-{4-[2-(4-dimethylamin-o-piperidin-1-yl)-ethoxy]-3-methoxy-phenyl}-pyridin-2-yl-amine, 6-[4-(2-dimethylamino-ethoxy)-3-ethoxy-phenyl]-pyridin-2-yl-amine, 6-[4-(2-pyrrolidinyl-ethoxy)-3-ethoxy-phenyl]-pyridin-2-yl-amine, 6-[4-(2-dimethylamino-ethoxy)-2-isopropyl-phenyl]-pyridin-2-yl-amine, 4-(6-amino-pyridin-yl)-3-cyclopropyl-phenol 6-[2-cyclopropyl-4-(2-dimethy-lamino-ethoxy)-phenyl]-pyridin-2-yl-amine, 6-[2-cyclopropyl-4-(2-pyrrolidin-1-yl-ethoxy)-phenyl]-pyridin-2-yl-amine, 3-[3-(6-amino-pyridin-2yl)-4-cycl-opropyl-phenoxy]-pyrrolidine-1-carboxylic acid tert-butyl ester 6-[2-cyclopropyl-4-(1-methyl-pyrrolidin-3-yl-oxy)-phenyl]-pyridin-2-yl-amine, 4-(6-amino-pyridin-2-yl)-3-cyclobutyl-phenol 6-[2-cyclobutyl-4-(2-dimethylamino-ethoxy)-phenyl]-pyridin-2-yl-amine, 6-[2-cyclobutyl-4-(2-pyrrolid-in-1-yl-ethoxy)-phenyl]-pyridin-2-yl-amine, 6-[2-cyclobutyl-4-(1-methyl-pyr-rolidin-3-yl-oxy)-phenyl]-pyridin-2-yl-amine, 4-(6-amino-pyridin-2-yl)-3-cy-clopentyl-phenol 6-[2-cyclopentyl-4-(2-dimethylamino-ethoxy)-phenyl]-pyrid-in-2-yl-amine, 6-[2-cyclopentyl-4-(2-pyrrolidin-1yl-ethoxy)-phenyl]-pyridin-2-yl-amine, 3-[4-(6-amino-pyridin-2yl)-3-methoxy-phenoxy]-pyrrolidine-1-ca-rboxylic acid tert butyl ester 6-[4-(1-methyl-pyrrolidin-3-yl-oxy)-2-metho-xy-phenyl]-pyridin-2-yl-amine, 4-[4-(6-amino-pyridin-2yl)-3-methoxy-phen-oxy-]-piperidine-1-carboxylic acid tert butyl ester 6-[2-methoxy-4-(1-methyl-p-iperidin-4-yl-oxy)-phenyl]-pyridin-2-yl-amine, 6-[4-(allyloxy)-2-methoxy-ph-enyl]-pyridin-2-yl-amine, 4-(6-amino-pyridin-2-yl)-3-methoxy-6-allyl-phenol 12 and 4-(6-amino-pyridin-2-yl)-3-methoxy-2-allyl-phenol 13 4-(6-amino-pyridin-2-yl)-3-methoxy-6-propyl-phenol 6-[4-(2-dimethylamino-ethoxy)-2-methoxy-5-propyl-phenyl]-pyridin-yl-amine, 6-[2-isopropyl-4-(pyrrolidin-3-yl-oxy)-phenyl]-pyridin-2-yl-amine, 6-[2-isopropyl-4-(piperidin-3-yl-oxy)-phenyl]-pyridin-2-yl-amine, 6-[2-isopropyl-4-(1-methyl-azetidin-3-yl-oxy)-phenyl]-pyridin-2-yl-amine, 6-[2-isopropyl-4-(1-methyl-piperidin-4-yl-oxy)-phenyl]-pyridin-2-yl-amine, 6-[2-isopropyl-4-(1-methyl-pyrrolidin-3-yl-oxy)-phenyl]-pyridin-2-yl-amin-e 6-[2-isopropyl-4-(1-methyl-pyrrolidin-3-yl-oxy)-phenyl]-pyridin-2-yl-amine, 6-[2-isopropyl-4-(2-methyl-2-aza-bicyclo[2.2.1]hept-5-yl-oxy)-phenyl]-p-yridin-2-yl-amine, 6-[4-(2-dimethylamino-ethoxy)-2-methoxy-phenyl]-pyridin-2-yl-amine, 6-{4-[2-(benzyl-methyl-amino)-ethoxy]-2-methoxy-phenyl}-pyridin-2-yl-amine, 6-[2-methoxy-4-(2-pyrrolidin-1-yl-ethoxy)-phenyl]-pyridin-2-yl-amine, 2-(6-amino-pyridin-2-yl)-5-(2-dimethylamino-ethoxy)-phenol 2-[4-(6-amino-pyridin-2-yl)-3-methoxy-phenoxy]-acetamide 6-[4-(2-amino-ethoxy)-2-methoxy-phenyl]-pyridin-2-yl-amine, 6-{4-[2-(3,4-dihydro-1h-isoquinolin-2-yl)-ethoxy]-2-methoxy-phenyl}-pyrid-in-2-yl-amine, 2-[4-(6-amino-pyridin-2-yl)-3-methoxy-phenoxy]-ethanol 6-{2-methoxy-4-[2-(2,2,6,6-tetramethyl-piperidin-1-yl)-ethoxy]-phenyl}-py-ridin-2-yl-amine, 6-{4-[2-(2,5-dimethyl-pyrrolidin-1-yl)-ethoxy]-2-methoxy-phenyl}-pyridin-2-yl-amine, 6-{4-[2-(2,5-dimethyl-pyrrolidin-1-yl)-ethoxy]-2-methoxy-phenyl}-pyridin-2-yl-amine, 2-[4-(6-amino-pyridin-2-yl)-3-methoxy-phenoxy]-1-(2,2,6,6-tetramethyl-piperidin-1-yl)-ethanone 6-[2-methoxy-4-(1-methyl-pyrrolidin-2-yl-methoxy)-phenyl]-pyridin-2-yl-amine, 6-[4-(2-dimethylamino-ethoxy)-2-propoxy-phenyl]-pyridin-2-yl-amine, 6-{4-[2-(benzyl-methyl-amino)-ethoxy]-2-propoxy-phenyl}-pyridin-2-yl-amin-e 6-[4-(2-ethoxy-ethoxy)-2-methoxy-phenyl]-pyridin-2-yl-amine, 6-[4-(2-dimethylamino-ethoxy)-2-isopropoxy-phenyl]-pyridin-2-yl-amine, 6-[4-(2-ethoxy-ethoxy)-2-isopropoxy-phenyl]-pyridin-2-yl-amine, 6-[2-methoxy-4-(3-methyl-butoxy)-phenyl]-pyridin-2-yl-amine, 6-[4-(2-dimethyl-amino-ethoxy)-2-ethoxy-phenyl]-pyridin-2-yl-amine, 6-{4-[2-(benzyl-methyl-amino)-ethoxy]-2-ethoxy-phenyl}-pyridin-2-yl-amine, 6-[2-ethoxy-4-(3-methyl-butoxy)-phenyl]-pyridin-2-yl-amine, 1-(6-amino-3-aza-bicyclo[3.1.0]hex-3-yl)-2-[4-(6-amino-pyridin-2-yl)-3-et-hoxy-phenoxy]-ethanone 6-[2-ethoxy-4-(2-pyrrolidin-1-yl-ethoxy)-phenyl]-py-ridin-2-yl-amine, 3-{2-[4-(6-amino-pyridin-2-yl)-3-ethoxy-phenoxy]-ethyl}-3-aza-bicyclo[3.1.0]hex-6-yl-amine, 1-(6-amino-3-aza-bicyclo[3.1.0]hex-3-yl)-2-[4-(6-amino-pyridin-2-yl)-3-methoxy-phenoxy]-ethanone 3-{2-[4-(6-amino-pyridin-2-yl)-3-methoxy-phenoxy]-ethyl}-3-aza-bicyclo[3-1.0]hex-6-yl-amine, 6-[2-isopropoxy-4-(2-pyrrolidin-1-yl-ethoxy)-phenyl]-py-ridin-2-yl-amine, 6-{4-[2-(benzyl-methyl-amino)-ethoxy]-2-isopropoxy-phenyl-}-pyridin-2-yl-amine, 6-[4-(2-dimethylamino-ethoxy)-2-methoxy-5-propyl-phen-yl]-pyridin-2-yl-amine, 6-[5-allyl-4-(2-dimethylamino-ethoxy)-2-methoxy-phe-nyl]-pyridin-2-yl-amine, 6-[5-allyl-2-methoxy-4-(2-pyrrolidin-1-yl-ethoxy)-phenyl]-pyridin-2-yl-amine, 6-[3-allyl-4-(2-dimethylamino-ethoxy)-2-methoxy-phenyl]-pyridin-2-yl-amine, 6-[2-methoxy-4-(pyrrolidin-3-yl-oxy)-phenyl]-p-yridin-2-yl-amine, 6-[2-methoxy-4-(1-methyl-pyrrolidin-3-yl-oxy)-phenyl]-py-ridin-2-yl-amine, 6-[2-ethoxy-4-(pyrrolidin-3-yl-oxy)-phenyl]-pyridin-2-yl-amine, 6-[2-isopropoxy-4-(pyrrolidin-3-yl-oxy)-phenyl]-pyridin-2-yl-amine, 6-[2-methoxy-4-(piperidin-4-yl-oxy)-phenyl]-pyridin-2-yl-amine, 6-[2-methoxy-4-(2,2,6,6-tetramethyl-piperidin-4-yl-oxy)-phenyl]-pyridin-2-yl-amine, 6-[2-isopropoxy-4-(pyrrolidin-3-yl-oxy)-phenyl]-pyridin-2-yl-amine, 3-[4-(6-amino-pyridin-2-yl)-3-methoxy-phenoxy]-azetidine-1-carboxylic acid tert-butyl ester 6-[4-(azetidin-3-yl-oxy)-2-methoxy-phenyl]-pyridin-2-yl-amine, 6-[2-methoxy-4-(1-methyl-azetidin-3-yl-oxy)-phenyl]-pyridin-2-y-1-amine, 6-[2-isopropoxy-4-(pyrrolidin-3-yl-oxy)-phenyl]-pyridin-2-yl-amine, 6-[2-isopropoxy-4-(pyrrolidin-3-yl-oxy)-phenyl]-pyridin-2-yl-amine, 6-[2-methoxy-4-(pyrrolidin-3-yl-oxy)-phenyl]-pyridin-2-yl-amine, 6-[2-methoxy-4-(1-methyl-pyrrolidin-3-yl-oxy)-phenyl]-pyridin-2-yl-amine, 6-[2-methoxy-4-(1-methyl-pyrrolidin-3-yl-oxy)-phenyl]-pyridin-2-yl-amine, 6-[2-methoxy-4-(2-methyl-2-aza-bicyclo[2.2.1]hept-5-yl-oxy)-phenyl]-pyrid-in-2-yl-amine, 6-[2-methoxy-4-(1-methyl-piperidin-4-yl-oxy)-phenyl]-pyridin-2-yl-amine, 6-[4-(1-ethyl-piperidin-4-yl-oxy)-2-methoxy-phenyl]-pyridin-2-yl-amine, 6-[5-allyl-2-methoxy-4-(1-methyl-pyrrolidin-3-yl-oxy)-phenyl]-pyr-idin-2-yl-amine, 6-[4-(2-dimethylamino-ethoxy)-2,6-dimethyl-phenyl]-pyridin-2-yl-amine, 6-[2,6-dimethyl-4-(3-piperidin-1-yl-propoxy)-phenyl]-pyridin-2-yl-amine, 642, 6-dimethyl-4-(2-pyrrolidin-1-yl-ethoxy)-phenyl-pyridin-2-yl-amine, 6-{2,6-dimethyl-4-[3-(4-methyl-piperazin-1-yl)-propoxy]-phenyl}-py-ridin-2-yl-amine, 6-[2-dimethyl-4-(2-morpholin-4-yl-ethoxy)-phenyl]-pyrid-in-2-yl-amine, 6-{4-[2-(benzyl-methyl-amino)-ethoxy]-2,6-dimethyl-phenyl}-p-yridin-2-yl-amine, 2-[4-(6-amino-pyridin-2-yl)-3,5-dimethyl-phenoxy]-acetam-ide 6-[4-(2-amino-ethoxy)-2,6-dimethyl-phenyl]-pyridin-2-yl-amine, 6-[2-isopropyl-4-(2-pyrrolidin-1-yl-ethoxy)-phenyl]-pyridin-2-yl-amine, 2-(2,5-dimethyl-pyrrolidin-1-yl)-6-[2-isopropyl-4-(2-pyrrolidin-1-yl-etho-xy)-phenyl]-pyridine 6-{4-[2-(3,5-dimethyl-piperidin-1-yl)-ethoxy]-2-isopr-opyl-phenyl}-pyridin-2-yl-amine, 6-[4-(2-dimethylamino-ethoxy)-2-isopropyl-phenyl]-pyridin-2-yl-amine, 6-[2-tert-butyl-4-(2-dimethylamino-ethoxy)-phen-yl]-pyridin-2-yl-amine, 6-[2-tert-butyl-4-(2-pyrrolidin-1-yl-ethoxy)-phenyl-]-pyridin-2-yl-amine, 6-[4-(2-pyrrolidinyl-ethoxy)-2,5-dimethyl-phen-yl]-pyr-idin-2-yl-amine, 6-[4-(2-dimethylamino-ethoxy)-2,5-dimethyl-phenyl]-pyridin-2-yl-amine, 6-[4-(2-(4-phenethylpiperazin-1-yl)-ethoxy)-2,5-dimethyl-pheny-1]-pyridin-2-yl-amine, 6-[2-cyclopropyl-4-(2-dimethylamino-1-methylethoxy)-phenyl]-pyridin-2-yl-amine, 6-[cyclobutyl-4-(2-dim- ethylamino-1-methyl-etho-xy)-phenyl]-pyridin-2-yl-amine, 6-[4-(allyloxy)-2-cyclobutyl-phenyl]-pyridi-n-2yl-amine, 2-allyl-4-(6-amino-pyridin-2-yl)-3-cyclobutyl-phenol and 2-allyl-4-(6-amino-pyridin-2-yl)-5-cyclobutyl-phenol 4-(6-amino-pyridin-2yl)-5-cyclobutyl-2-propyl-phenol 4-(6-amino-pyridin-2yl)-3-cyclobutyl-2-propyl-phenol 6-[2-cyclobutyl-4-(2-dimethylamino-1-methyl-ethoxy)-5-propyl-phenyl]-pyri-din-2-yl-amine, 6-[2-cyclobutyl-4-(2-dimethylamino-1-methyl-ethoxy)-3-propy-1-phenyl]-pyridin-2-yl-amine, 6-[2-cyclobutyl-4-(2-dimethylamino-ethoxy)-5-propyl-phenyl]-pyridin-2-yl-amine, 6-[2-cyclobutyl- 4-(2-dimethylamino-ethox-y)-3-propyl-phenyl]-pyridin-2-yl-amine, 6-[2-cyclobutyl-4-(1-methyl-pyrroli-din-3-yl-oxy)-5-propyl-phenyl]-pyridin-2-yl-amine, 6-[cyclobutyl-4-(1-methy-1-pyrrolidin-3-yl-oxy)-3-propyl-phenyl]-pyridin-2-yl-amine, 2-(4-benzyloxy-5-hydroxy-2-methoxy-phenyl)-6-(2,5-dimethyl-pyrrol-1-yl)-p-yridine 6-[4-(2-dimethy-lamino-ethoxy)-5-ethoxy-2-methoxy-phenyl]-pyridin-2-yl-amine, 6-[5-ethyl-2-methoxy-4-(1-methyl-piperidin-4-yl-oxy)-phenyl]-pyr-idin-2-yl-amine, 6-[5-ethyl-2-methoxy-4-(piperidin-4-yl-oxy)-phenyl]-pyridi-n-2-yl-amine, 6-[2,5-dimethoxy-4-(1-methyl-pyrrolidin-3-yl-oxy)-phenyl]-pyr-idin-2-yl-amine, 6-[4-(2-dimethylamino-ethoxy)-5-ethyl-2-methoxy-phenyl]-py-ridin-2-yl-amine.

Exemplary NMDA receptor antagonist include (+)-(1S, 2S)-1-(4-hydroxy-phenyl)-2-(4-hydroxy-4-phenylpiperi-dino)-1-pro-panol, (1S, 2S)-1-(4-hydroxy-3-methoxyphe-nyl)-2-(4-hydroxy-4-phenylpiperi-dino)-1-propanol, (3R, 4S)-3-(4-(4-fluorophenyl)-4-hydroxypiperidin-1-yl-)-chro-man-4,7-diol, (1R*, 2R*)-1-(4-hydroxy-3-methylphenyl)-2-(4-(4-fluoro-phenyl)-4-hydroxypiperidin-1-yl)-propan-1-ol-mesylate or a pharmaceutically acceptable acid addition salt thereof.

Exemplary dopamine agonists include ropininole; L-dopa decarboxylase inhibitors such as carbidopa or benserazide, bromocriptine, dihydroergocryptine, etisulergine, AF-14, alaptide, pergolide, piribedil; dopamine D1 receptor ago-nists such as A-68939, A-77636, dihydrexine, and SKF-38393; dopamine D2 receptor agonists such as carbergoline, lisuride, N-0434, naxagolide, PD-118440, pramipexole, quinpirole and ropinirole; dopamine/beta-adrenegeric recep-tor agonists such as DPDMS and dopexamine; dopamine/5-HT uptake inhibitor/5-HT-1A agonists such as roxindole; dopamine/opiate receptor agonists such as NIH-10494; alpha 2-adrenergic antagonist/dopamine agonists such as terguride; alpha 2-adrenergic antagonist/dopamine D2 ago-nists such as ergolines and talipexole; dopamine uptake inhibitors such as GBR-12909, GBR-13069, GYKI-52895, and NS-2141; monoamine oxidase-B inhibitors such as selegiline, N-(2-butyl)-N-methylpropargylamine, N-methyl-N-(2-pentyl)propargylamine, AGN-1133, ergot derivatives, lazabemide, LU-53439, MD-280040 and mofegiline; and COMT inhibitors such as CGP-28014.

Exemplary acetyl cholinesterase inhibitors include donepizil, 1-(2-methyl-1H-benzimida-zol-5-yl)-3-[1-(phe-nylmethyl)-4-piperidinyl]-1-propanone; 1-(2-phenyl-1H-benzimidazol-5-yl)-3-[1-(phenylmethyl)-4-piperidinyl]-1-pr-opanone; 1-(1-ethyl-2-methyl-1H-benzimidazol-5-yl)-3-[1-(phenylmethyl)-4-p-iperidinyl]-1-propanone; 1-(2-met-hyl-6-benzothiazolyl)-3-[1-(phenylmethyl)-4-piperidinyl]-1-propanone; 1-(2-methyl-6-benzothiazolyl)-3-[1-[(2-met-hyl-4-thiazolyl)methyl]-4-piperidinyl]-1-propanone; 1-(5-methyl-benzo[b]thie-n-2-yl)-3-[1-(phenylmethyl)-4-piper-idinyl]-1-propanone; 1-(6-methyl-benzo[b]thien-2-yl)-3-[1-(phenylmethyl)-4-piperidinyl]-1-prop-anone; 1-(3,5-dim-ethyl-benzo[b]thien-2-yl)-3-[1-(phenylmethyl)-4-piperidin-yl]-1-propanone; 1-(benzo[b]thien-2-yl)-3-[1-(phenylm-ethyl)-4-piperidinyl]-1-propanone; 1-(benzofuran-2-yl)-3-[1-(phenylmethyl)-4-piperidinyl]-1-pro-panone; 1-(1-phenylsulfonyl-6-methyl-indol-2-yl)-3-[1-(phenylmethyl)-4-pip-eridinyl]-1-propanone; 1-(6-methyl-indol-2-yl)-3-[1-(phenylmethyl)-4-piper-idinyl]-1-propanone; 1-(1-pheny-lsulfonyl-5-amino-indol-2-yl)-3-[1-(phenylm-ethyl)-4-pip-eridinyl]-1-propanone; 1-(5-amino-indol-2-yl)-3-[1-(phe-nylmethyl-hyl)-4-piperidinyl]-1-propanone; and 1-(5-acety-lamino-indol-2-yl)-3-[1-(ph-enylmethyl)-4-piperidinyl]-1-propanone; 1-(6-quinolyl)-3-[1-(phenylmethyl)-4-piper-idinyl]-1-propanone; 1-(5-indolyl)-3-[1-(phenylmethyl)-4-piperidiny-1]-1-propanone; 1-(5-benzthienyl)-3-[1-(phenyl-methyl)-4-piperidinyl]-1-pro-panone; 1-(6-quinazolyl)-3-[1-(phenylmethyl)-4-piperidinyl]-1-propanone; 1-(6-benzoxazolyl)-3-[1-(phenylmethyl)-4-piperidinyl]-1-propanone; 1-(5-benzofuranyl)-3-[1-(phenylmethyl)-4-piperidinyl]-1-propanone; 1-(5-methyl-benzimidazol-2-yl)-3-[1-(phenylmethyl)-4-piperidinyl]-1-propa-none; 1-(6-me-thyl-benzimidazol-2-yl)-3-[1-(phenylmethyl)-4-piperidi-nyl]-1-propanone; 1-(5-chloro-benzo[b]thien-2-yl)-3-[1-(phenylmethyl)-4-piperidin-yl]-1-propanone; 1-(5-azaindol-2-yl)-3-[1-(phenylmethyl)-4-piperidinyl]-1-p-ropanone; 1-(6-azabenzo[b]thien-2-yl)-3-[1-(phenylmethyl)-4-piper-idinyl]-1-propanone; 1-(1H-2-oxo-pyrrolo[2', 3', 5,6]benzo[b]thieno-2-yl)-3-[1-(phenylmethyl)-4-piperidinyl]-1-pro-panone; 1-(6-methyl-benzothiazol-2-yl)-3-[1-(pheny-lmethyl)-4-piperidinyl]-1-propanone; 1-(6-methoxy-indol-2-yl)-3-[1-(phenylmethyl)-4-piperidinyl]-1-propanone; 1-(6-methoxy-benzo[b]thien-2-yl)-3-[1-(phenylmethyl)-4-piperidinyl]-1-pro-panone; 1-(6-acetylamino-benzo[b]thi-en-2-yl)-3-[1-(phenylmethyl)-4-piperid-inyl]-1-propanone; 1-(5-acetylamino-benzo[b]thien-2-yl)-3-[1-(phenylmet-hyl-)-4-piperidinyl]-1-propanone; 6-hydroxy-3-[2-[1-(phe-nylmethyl)-4-piperidin-yl]ethyl]-1,2-benzisoxazole; 5-methyl-3-[2-[1-(phenylmethyl)-4-piperidinyl-]ethyl]-1,2-benzisoxazole; 6-methoxy-3 [2-[1-(phenylmethyl)-4-piper-idinyl]et-hyl]-1,2-benzisoxazole; 6-acetamide-3-[2-[1-(phe-nylmethyl)-4-piperidinyl]-ethyl]-1,2-benzisoxazole; 6-amino-3-[2-[1-(phenymethyl)-4-piperidinyl]ethy-1]-1,2-benzisoxazole; 6-(4-morpholinyl)-3-[2-[1-(phenylmethyl)-4-piperidin-yl]ethyl]-1,2-benzisoxazole; 5,7-dihydro-3-[2-[1-(phenylmethyl)-4-piperidi-nyl]ethyl]-6H-pyrrolo[4,5-f]-1,2-benzisoxazol-6-one; 3-[2-[1-(phenylmethyl)-4-piperi-dinyl]ethyl]-1,2-benzisothiazole; 3-[2-[1-(phenylmethyl)-4-piperidinyl]ethenyl]-1,2-benzisoxazole; 6-phenylamino-3-[2-[1-(phenylmethyl)-4-piperidinyl]ethyl]-1,2,-benzisoxaz-ole; 6-(2-thiazoly)-3-[2-[1-(phenylmethyl)-4-piperidinyl]ethyl]-1,2-benzis-oxazole; 6-(2-oxazolyl)-3-[2-[1-(phe-nylmethyl)-4-piperidinyl]ethyl]-1,2-be-nzisoxazole; 6-pyr-rolidinyl-3-[2-[1-(phenylmethyl)-4-piperidinyl]ethyl]-1,-2-benzisoxazole; 5,7-dihydro-5,5-dimethyl-3-[2-[1-(phenylm-ethyl)-4-piperid-inyl]ethyl]-6H-pyrrolo[4,5-f]-1,2-benzisoxazole-6-one; 6,8-dihydro-3-[2-[1-(phenylmethyl)-4-piperidinyl]ethyl]-7H-pyrrolo[5,4-g]-1,2-benzisoxazole-7-one; 3-[2-[1-(phenylmethyl)-4-piperidinyl]ethyl]-5,6,-8-trihydro-7H-isoxazolo[4,5-g]-quinolin-7-one; 1-benzyl-4-((5,6-dimethoxy-1-indanon)-2-yl)methylpiperidine, 1-benzyl-4-((5,6-dimethoxy-1-indanon)-2-ylidenyl)methyl-piperidine, 1-benzyl-4-((5-methoxy-1-indanon)-2-yl)meth-ylp-iperidine, 1-benzyl-4-((5,6-diethoxy-1-indanon)-2-yl)methylpiperidine, 1-benzyl-4-((5,6-methnylenedioxy-1-indanon)-2-yl)methylpiperidine, 1-(m-nitrobenzyl)-4-((5,6-dimethoxy-1-indanon)-2-yl)methylpiperidine, 1-cycl-ohexymethyl-4-((5,6-dimethoxy-1-indanon)-2-yl)methylpi-peridine, 1-(m-florobenzyl)-4-((5,6-dimethoxy-1-indanon)-2-yl)methylpiperidine, 1-benzyl-4-((5,6-dimethoxy-1-in-danon)-2-yl)propylpiperidine, and 1-benzyl-4-((5-isopropoxy-6-methoxy-1-indanon)-2-yl)methylpiperidine.

Exemplary calcium channel antagonists include dilti-azem, omega-conotoxin GVIA, methoxyverapamil, amlo-dipine, felodipine, lacidipine, and mibefradil.

Exemplary GABA-A receptor modulators include clom-ethiazole; IDDB; gaboxadol (4,5,6,7-tetrahydroisoxazolo[5,4-c]pyridin-3-ol); ganaxolone (3-alpha-hydroxy-3-beta-methyl-5-alpha-pregnan-20-one); fengabine (2-

[(butylimino)-(2-chlorophenyl)methyl]-4-chlorophenol); 2-(4-methoxyphenyl)-2,5,6,7,8,9-hexahydro-pyrazolo[4,3-c]cinnolin-3-one; 7-cyclobutyl-6-(2-methyl-2H-1,2,4-triazol-3-ylmethoxy)-3-phenyl-1,2,4-triazolo[4,3-]pyridazine; (3-fluoro-4-methylphenyl)-N-({-1-[(2-methylphenyl) methyl]-benzimidazol-2-yl}1methyl)-N-pentylcarboxamide; and 3-(aminomethyl)-5-methylhexanoic acid.

Exemplary potassium channel openers include diazoxide, flupirtine, pinacidil, levcromakalim, rilmakalim, chromakalim, PCO-400 and SKP-450 (2-[2"(1", 3"-dioxolone)-2-methyl]-4-(2'-oxo-1'-pyrrolidinyl)-6-nitro-2H-1-benzopyran).

Exemplary AMPA/kainate receptor antagonists include 6-cyano-7-nitroquinoxalin-2,3-di-one (CNQX); 6-nitro-7-sulphamoylbenzo[f]quinoxaline-2,3-dione (NBQX); 6,7-dinitroquinoxaline-2,3-dione (DNQX); 1-(4-aminophenyl)-4-methyl-7,8-m-ethylenedioxy-5H-2,3-benzodiazepine hydrochloride; and 2,3-dihydroxy-6-nitro-7-sulfamoyl-benzo-[f]quinoxaline.

Exemplary sodium channel antagonists include ajmaline, procainamide, flecainide and riluzole.

Exemplary matrix-metalloprotease inhibitors include 4-[4-(4-fluorophenoxy)benzenesulfonylamino]tetrahydro-pyran-4-carboxylic acid hydroxyamide; 5-Methyl-5-(4-(4'-fluorophenoxy)-phenoxy)-pyrimidine-2,4,6-trione; 5-n-Butyl-5-(4-(4'-fluorophenoxy)-phenoxy)-pyrimidine-2,4,6-trione and prinomistat.

Exemplary inhibitors of p38 MAP kinase and c-jun-N-terminal kinases include pyridyl imidazoles, such as PD 169316, isomeric PD 169316, SB 203580, SB 202190, SB 220026, and RWJ 67657. Others are described in U.S. Pat. No. 6,288,089, and incorporated by reference herein.

In an exemplary embodiment, a combination therapy for treating or preventing MS comprises a therapeutically effective amount of a nicotinamide riboside chloride preparation or pharmaceutical composition of the invention that increase the level of NAD and/or activity of a sirtuin protein and one or more of Avonex® (interferon beta-1a), Tysabri® (natalizumab), or Fumaderm® (BG-12/Oral Fumarate).

In another embodiment, a combination therapy for treating or preventing diabetic neuropathy or conditions associated therewith comprises a therapeutically effective amount of a nicotinamide riboside chloride preparation or pharmaceutical composition of the invention that increase the level of NAD and/or activity of a sirtuin protein and one or more of tricyclic antidepressants (TCAs) (including, for example, imipramine, amytriptyline, desipramine and nortriptyline), serotonin reuptake inhibitors (SSRIs) (including, for example, fluoxetine, paroxetine, sertralene, and citalopram) and antiepileptic drugs (AEDs) (including, for example, gabapentin, carbamazepine, and topimirate).

Blood Coagulation Disorders

In other aspects, nicotinamide riboside chloride preparations and pharmaceutical compositions of the invention that increase the level of NAD and/or activity of a sirtuin protein can be used to treat or prevent blood coagulation disorders (or hemostatic disorders). As used interchangeably herein, the terms "hemostasis", "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. After initiation of clotting, blood coagulation proceeds through the sequential activation of certain plasma proenzymes to their enzyme forms (see, for example, Coleman, R. W. et al. (eds.) Hemostasis and Thrombosis, Second Edition, (1987)). These plasma glycoproteins, including Factor XII, Factor XI, Factor IX, Factor X, Factor VII, and prothrombin, are zymogens of serine proteases. Most of these blood clotting enzymes are effective on a physiological scale only when assembled in complexes on membrane surfaces with protein cofactors such as Factor VIII and Factor V. Other blood factors modulate and localize clot formation, or dissolve blood clots. Activated protein C is a specific enzyme that inactivates procoagulant components. Calcium ions are involved in many of the component reactions. Blood coagulation follows either the intrinsic pathway, where all of the protein components are present in blood, or the extrinsic pathway, where the cell-membrane protein tissue factor plays a critical role. Clot formation occurs when fibrinogen is cleaved by thrombin to form fibrin. Blood clots are composed of activated platelets and fibrin.

Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place. It involves a cascade of complicated and regulated biochemical reactions between circulating blood proteins (coagulation factors), blood cells (in particular platelets), and elements of an injured vessel wall.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering a nicotinamide riboside chloride preparation or pharmaceutical composition of the invention that increases the level of NAD and/or activity of a sirtuin protein. The compositions and methods disclosed herein are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include diseases or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites. Examples of thrombotic disorders include, but are not limited to, thromboembolism, deep vein thrombosis, pulmonary embolism, stroke, myocardial infarction, miscarriage, thrombophilia associated with anti-thrombin III deficiency, protein C deficiency, protein S deficiency, resistance to activated protein C, dysfibrinogenemia, fibrinolytic disorders, homocystinuria, pregnancy, inflammatory disorders, myeloproliferative disorders, arteriosclerosis, angina, e.g., unstable angina, disseminated intravascular coagulation, thrombotic thrombocytopenic purpura, cancer metastasis, sickle cell disease, glomerular nephritis, and drug induced thrombocytopenia (including, for example, heparin induced thrombocytopenia). In addition, nicotinamide riboside chloride preparations and pharmaceutical compositions of the invention that increase the level of NAD and/or activity of a sirtuin protein may be administered to prevent thrombotic events or to prevent re-occlusion during or after therapeutic clot lysis or procedures such as angioplasty or surgery.

In another embodiment, a combination drug regimen may include drugs or compounds for the treatment or prevention of blood coagulation disorders or secondary conditions associated with these conditions. Thus, a combination drug regimen may include a nicotinamide riboside chloride preparation or pharmaceutical composition of the invention that increases the level of NAD and/or activity of a sirtuin protein and one or more anti-coagulation or anti-thrombosis agents. For example, one or more nicotinamide riboside chloride preparations or pharmaceutical compositions can be combined with an effective amount of one or more of: aspirin, heparin, and oral Warfarin that inhibits Vit K-dependent factors, low molecular weight heparins that inhibit factors X and II, thrombin inhibitors, inhibitors of platelet GP IIbIIIa receptors, inhibitors of tissue factor (TF), inhibitors of human von Willebrand factor, inhibitors of one or more factors involved in hemostasis (in particular in the coagulation cascade). In addition, nicotinamide riboside chloride preparations or pharmaceutical compositions of the invention that increase the level of NAD and/or activity of a sirtuin protein can be combined with thrombolytic agents, such as t-PA, streptokinase, reptilase, TNK-t-PA, and staphylokinase.

Weight Control

In another aspect, nicotinamide riboside chloride preparations and pharmaceutical compositions of the invention that increase the level of NAD and/or the activity of a sirtuin protein may be used for treating or preventing weight gain or obesity in a subject. For example, nicotinamide riboside chloride preparations and pharmaceutical compositions of the invention that increase the level of NAD and/or activity of a sirtuin protein may be used, for example, to treat or prevent hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, nicotinamide riboside chloride preparations and pharmaceutical compositions of the invention that increase the level of NAD and/or activity of a sirtuin protein may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self esteem). Stunkard A. J., Wadden T. A. (Editors) Obesity: theory and therapy, Second Edition. New York: Raven Press, 1993. Finally, patients with AIDS can develop lipodystrophy or insulin resistance in response to combination therapies for AIDS.

In another embodiment, nicotinamide riboside chloride preparations and pharmaceutical compositions of the invention that increase the level of NAD and/or activity of a sirtuin protein may be used for inhibiting adipogenesis or fat cell differentiation, whether in vitro or in vivo. In particular, high circulating levels of insulin and/or insulin like growth factor (IGF) 1 will be prevented from recruiting preadipocytes to differentiate into adipocytes. Such methods may be used for treating or preventing obesity.

In other embodiments, nicotinamide riboside chloride preparations and pharmaceutical compositions of the invention that increase the level of NAD and/or activity of a sirtuin protein may be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In other embodiments, nicotinamide riboside chloride preparations and pharmaceutical compositions of the invention may be used to treat a subject who has cachexia or may be likely to develop cachexia. A combination of agents may also be administered. A method may further comprise monitoring in the subject the state of the disease or the level of NAD and/or the of activation of sirtuins, for example, in adipose tissue. Methods for promoting appetite and/or weight gain may include, for example, prior identifying a subject as being in need of decreased fat or lipid metabolism, e.g., by weighing the subject, determining the BMI of the subject, or evaluating fat content of the subject or sirtuin activity in cells of the subject. The method may also include monitoring the subject, e.g., during and/or after administration of the nicotinamide riboside chloride preparations and pharmaceutical compositions of the invention. The administering can include one or more dosages, e.g., delivered in boluses or continuously. Monitoring can include evaluating a hormone or a metabolite. Exemplary hormones include leptin, adiponectin, resistin, and insulin. Exemplary metabolites include triglyercides, cholesterol, and fatty acids.

A method for modulating weight may further comprise monitoring the weight of the subject and/or the level of NAD (e.g. intracellular NAD levels, levels of NAD in tissues or plasma, and/or overall NAD levels in an organism) and/or modulation of sirtuins, for example, in adipose tissue.

In an exemplary embodiment, a nicotinamide riboside chloride preparation or pharmaceutical composition of the invention that increased the level of NAD and/or the activity of a sirtuin protein may be administered as a combination therapy for treating or preventing weight gain or obesity. For example, one or more nicotinamide riboside chloride preparations or pharmaceutical compositions of the invention that increase the level of NAD and/or activity of a sirtuin protein may be administered in combination with one or more anti-obesity agents. Exemplary anti-obesity agents include, for example, phenylpropanolamine, ephedrine, pseudoephedrine, phentermine, a cholecystokinin-A agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (leptin), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

In another embodiment, nicotinamide riboside chloride preparations and pharmaceutical compositions of the invention that increase the level of NAD and/or activity of a sirtuin protein may be administered to reduce drug-induced weight gain. For example, a nicotinamide riboside chloride preparation or pharmaceutical composition of the invention that increases the level of NAD and/or activity of a sirtuin protein may be administered as a combination therapy with medications that may stimulate appetite or cause weight gain, in particular, weight gain due to factors other than water retention. Examples of medications that may cause weight gain, include for example, diabetes treatments, including, for example, sulfonylureas (such as glipizide and glyburide), thiazolidinediones (such as pioglitazone and rosiglitazone), meglitinides, nateglinide, repaglinide, sulphonylurea medicines, and insulin; anti-depressants, including, for example, tricyclic antidepressants (such as amitriptyline and imipramine), irreversible monoamine oxidase inhibitors (MAOIs), selective serotonin reuptake inhibitors (SSRIs), bupropion, paroxetine, and mirtazapine; steroids, such as, for example, prednisone; hormone therapy; lithium carbonate; valproic acid; carbamazepine; chlorpromazine; thiothixene; beta blockers (such as propranolo); alpha blockers (such as clonidine, prazosin and terazosin); and contraceptives including oral contraceptives (birth control pills) or other contraceptives containing estrogen and/or progesterone (Depo-Provera, Norplant, Ortho), testosterone or Megestrol. In another exemplary embodiment, nicotinamide riboside chloride preparations and pharmaceutical compositions of the invention that increase the level of NAD and/or the activity of a sirtuin protein may be administered as part of a smoking cessation program to prevent weight gain or reduce weight already gained.

Metabolic Disorders/Diabetes

In another aspect, nicotinamide riboside chloride preparations and pharmaceutical compositions of the invention that increase the level of NAD and/or activity of a sirtuin protein may be used for treating or preventing a metabolic disorder, such as insulin-resistance, a pre-diabetic state, type II diabetes, and/or complications thereof. Administration of a nicotinamide riboside chloride preparation or pharmaceutical composition of the invention that increases the level of NAD and/or activity of a sirtuin protein may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

In an exemplary embodiment, nicotinamide riboside chloride preparations and pharmaceutical compositions of the invention that increase the level of NAD and/or activity of a sirtuin protein may be administered as a combination therapy for treating or preventing a metabolic disorder. For example, one or more nicotinamide riboside chloride preparation or pharmaceutical composition of the invention that increases the level of NAD and/or activity of a sirtuin protein may be administered in combination with one or more anti-diabetic agents. Exemplary anti-diabetic agents include, for example, an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a peroxisome proliferator-activated receptor-γ (PPAR-γ) ligand such as troglitazone, rosaglitazone, pioglitazone or GW-1929, a sulfonylurea, glipazide, glyburide, or chlorpropamide wherein the amounts of the first and second compounds result in a therapeutic effect. Other anti-diabetic agents include a glucosidase inhibitor, a glucagon-like peptide-1 (GLP-1), insulin, a PPAR α/γ dual agonist, a meglitinide and an αP2 inhibitor. In an exemplary embodiment, an anti-diabetic agent may be a dipeptidyl peptidase IV (DP-IV or DPP-IV) inhibitor, such as, for example LAF237 from Novartis (NVP DPP728; 1-[[[2-[(5-cyanopyridin-2-yl)amino]ethyl]amino]acetyl]-2-cyano-(S)-pyrrolidine) or MK-04301 from Merck (see e.g., Hughes et al., Biochemistry 38: 11597-603 (1999)).

Inflammatory Diseases

In other aspects, nicotinamide riboside chloride preparations and pharmaceutical compositions of the invention that increase the level of NAD and/or activity of a sirtuin protein can be used to treat or prevent a disease or disorder associated with inflammation. Nicotinamide riboside chloride preparations and pharmaceutical compositions of the invention that increase the level of NAD and/or activity of a sirtuin protein may be administered prior to the onset of, at, or after the initiation of inflammation. When used prophylactically, the compositions are preferably provided in advance of any inflammatory response or symptom. Administration of the compositions may prevent or attenuate inflammatory responses or symptoms.

Exemplary inflammatory conditions include, for example, multiple sclerosis, rheumatoid arthritis, psoriatic arthritis, degenerative joint disease, spondouloarthropathies, gouty arthritis, systemic lupus erythematosus, juvenile arthritis, rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, scleroderma, psoriasis, and dermatosis with acute inflammatory components.

In another embodiment, nicotinamide riboside chloride preparations and pharmaceutical compositions of the invention that increase the level of NAD and/or activity of a sirtuin protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, nicotinamide riboside chloride preparations and pharmaceutical compositions of the invention that increase the level of NAD and/or the activity of a sirtuin protein may be used to treat autoimmune diseases and/or inflammation associated with autoimmune diseases such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In certain embodiments, one or more nicotinamide riboside chloride preparations or pharmaceutical compositions of the invention that increase the level of NAD and/or the activity of a sirtuin protein may be taken alone or in combination with other compounds useful for treating or preventing inflammation. Exemplary anti-inflammatory agents include, for example, steroids (e.g., cortisol, cortisone, fludrocortisone, prednisone, 6-alpha-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other therapeutic agent is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, .alpha.-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, carprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, coproprolamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocortolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydrocortamate, hydrocortisone, hydrocortisone acetate, hydrocortisone succinate, hydrocortisone hemi succinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicyl sulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In an exemplary embodiment, a nicotinamide riboside chloride preparation or pharmaceutical composition of the invention that increases the level of NAD and/or the activity of a sirtuin protein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, lumiracoxib, 2-(3,5-difluorophenyl)-3-[4-(methylsulfonyl)phenyl]-2-cyclopenten-1-one, (S)-6,8-dichloro-2-(trifluoromethyl)-2H-1-benzopyran-3-carboxylic acid, 2-(3,4-difluorophenyl)-4-(3-hydroxy-3-methyl-1-butoxy)-5-[4-(methylsulfonyl)phenyl]-3-(2H)-pyridazinone, 4-[5-(4-fluorophenyl)-3-(trifluoromethyl)-1H-pyrazol-1-yl]benzenesulfonamide, tert-butyl 1 benzyl-4-[(4-oxopiperidin-1-yl}sulfonyl]piperidine-4-carboxylate, 4-[5-(phenyl)-3-(trifluoromethyl)-1H-pyrazol-1-yl]benzenesulfonamide, salts and prodrugs thereof.

Flushing

In another aspect, nicotinamide riboside chloride preparations and pharmaceutical compositions of the invention that increase the level of NAD and/or the activity of a sirtuin protein may be used for reducing the incidence or severity of flushing and/or hot flashes which are symptoms of a disorder. For instance, the subject method includes the use of nicotinamide riboside chloride preparations and pharmaceutical compositions of the invention that increase the level of NAD and/or the activity of a sirtuin protein, alone or in combination with other agents, for reducing incidence or severity of flushing and/or hot flashes in cancer patients. In other embodiments, the method provides for the use of nicotinamide riboside chloride preparations and pharmaceutical compositions of the invention that increase the level of NAD and/or activity of a sirtuin protein to reduce the incidence or severity of flushing and/or hot flashes in menopausal and post-menopausal woman.

In another aspect, nicotinamide riboside chloride preparations and pharmaceutical compositions of the invention that increase the level of NAD and/or the activity of a sirtuin protein may be used as a therapy for reducing the incidence or severity of flushing and/or hot flashes which are side-effects of another drug therapy, e.g., drug-induced flushing. In certain embodiments, a method for treating and/or preventing drug-induced flushing comprises administering to a patient in need thereof a formulation comprising at least one flushing inducing compound and at least one nicotinamide riboside chloride preparation or pharmaceutical composition of the invention that increases the level of NAD and/or activity of a sirtuin protein. In other embodiments, a method for treating drug induced flushing comprises separately administering one or more compounds that induce flushing and one or more nicotinamide riboside chloride preparation or pharmaceutical composition of the invention, e.g., wherein the nicotinamide riboside chloride preparation or pharmaceutical composition of the invention and flushing inducing agent have not been formulated in the same compositions. When using separate formulations, the nicotinamide riboside chloride may be administered (1) at the same as administration of the flushing inducing agent, (2) intermittently with the flushing inducing agent, (3) staggered relative to administration of the flushing inducing agent, (4) prior to administration of the flushing inducing agent, (5) subsequent to administration of the flushing inducing agent, and (6) various combination thereof. Exemplary flushing inducing agents include, for example, niacin, faloxifene, antidepressants, anti-psychotics, chemotherapeutics, calcium channel blockers, and antibiotics.

In one embodiment, nicotinamide riboside chloride preparations and pharmaceutical compositions of the invention that increase the level of NAD and/or the activity of a sirtuin protein may be used to reduce flushing side effects of a vasodilator or an antilipemic agent (including anticholesteremic agents and lipotropic agents). In an exemplary embodiment, a nicotinamide riboside chloride preparation or pharmaceutical composition of the invention that increases the level of NAD and/or activity of a sirtuin protein may be used to reduce flushing associated with the administration of niacin.

Nicotinic acid, 3-pyridinecarboxylic acid or niacin, is an antilipidemic agent that is marketed under, for example, the trade names Nicolar®, SloNiacin®, Nicobid® and Time Release Niacin®. Nicotinic acid has been used for many years in the treatment of lipidemic disorders such as hyperlipidemia, hypercholesterolemia and atherosclerosis. This compound has long been known to exhibit the beneficial effects of reducing total cholesterol, low density lipoproteins or "LDL cholesterol," triglycerides and apolipoprotein a (Lp(a)) in the human body, while increasing desirable high density lipoproteins or "HDL cholesterol".

Typical doses range from about 1 gram to about 3 grams daily. Nicotinic acid is normally administered two to four times per day after meals, depending upon the dosage form selected. Nicotinic acid is currently commercially available in two dosage forms. One dosage form is an immediate or rapid release tablet which should be administered three or four times per day. Immediate release ("IR") nicotinic acid formulations generally release nearly all of their nicotinic acid within about 30 to 60 minutes following ingestion. The other dosage form is a sustained release form which is suitable for administration two to four times per day. In contrast to IR formulations, sustained release ("SR") nicotinic acid formulations are designed to release significant quantities of drug for absorption into the blood stream over specific timed intervals in order to maintain therapeutic levels of nicotinic acid over an extended period such as 12 or 24 hours after ingestion.

As used herein, the term "nicotinic acid" is meant to encompass nicotinic acid or a compound other than nicotinic acid itself which the body metabolizes into nicotinic acid, thus producing essentially the same effect as nicotinic acid. Exemplary compounds that produce an effect similar to that of nicotinic acid include, for example, nicotinyl alcohol tartrate, d-glucitol hexanicotinate, aluminum nicotinate, niceritrol and d,l-alpha-tocopheryl nicotinate. Each such compound will be collectively referred to herein as "nicotinic acid."

In another embodiment, the invention provides a method for treating and/or preventing hyperlipidemia with reduced flushing side effects. The method comprises the steps of administering to a subject in need thereof a therapeutically effective amount of nicotinic acid and a nicotinamide riboside chloride preparation or pharmaceutical composition of the invention that increases the level of NAD and/or activity of a sirtuin protein in an amount sufficient to reduce flushing. In an exemplary embodiment, the nicotinic acid and/or the nicotinamide riboside chloride preparation or pharmaceutical composition of the invention may be administered nocturnally.

In another representative embodiment, the method involves the use of nicotinamide riboside chloride preparations and pharmaceutical compositions of the invention that increase the level of NAD and/or activity of a sirtuin protein to reduce flushing side effects of raloxifene. Raloxifene acts like estrogen in certain places in the body, but is not a hormone. It helps prevent osteoporosis in women who have reached menopause. Osteoporosis causes bones to gradually grow thin, fragile, and more likely to break. Evista slows down the loss of bone mass that occurs with menopause, lowering the risk of spine fractures due to osteoporosis. A common side effect of raloxifene is hot flashes (sweating and flushing). This can be uncomfortable for women who already have hot flashes due to menopause.

In another representative embodiment, the method involves the use of nicotinamide riboside chloride preparations and pharmaceutical compositions of the invention that increase the level of NAD and/or the activity of a sirtuin protein to reduce flushing side effects of antidepressants or anti-psychotic agent. For instance, nicotinamide riboside chloride preparations and pharmaceutical compositions of the invention that increase the level of NAD and/or activity of a sirtuin protein can be used in conjunction (administered separately or together) with a serotonin reuptake inhibitor, a 5HT2 receptor antagonist, an anticonvulsant, a norepinephrine reuptake inhibitor, an alpha-adrenoreceptor antagonist, an NK-3 antagonist, an NK-1 receptor antagonist, a PDE4 inhibitor, an Neuropeptide Y5 Receptor Antagonists, a D4 receptor antagonist, a 5HT1A receptor antagonist, a 5HT1D receptor antagonist, a CRF antagonist, a monoamine oxidase inhibitor, or a sedative-hypnotic drug.

In certain embodiments, nicotinamide riboside chloride preparations and pharmaceutical compositions of the invention that increase the level of NAD and/or the activity of a sirtuin protein may be used as part of a treatment with a serotonin reuptake inhibitor (SRI) to reduce flushing. In certain preferred embodiments, the SRI is a selective serotonin reuptake inhibitor (SSRI), such as a fluoxetinoid (fluoxetine, norfluoxetine) or a nefazodonoid (nefazodone, hydroxynefazodone, oxonefazodone). Other exemplary SSRI's include duloxetine, venlafaxine, milnacipran, citalopram, fluvoxamine, paroxetine and sertraline. The nicotinamide riboside chloride preparations and pharmaceutical compositions of the invention that increase the level of NAD and/or the activity of a sirtuin protein can also be used as part of a treatment with sedative-hypnotic drug, such as selected from the group consisting of a benzodiazepine (such as alprazolam, chlordiazepoxide, clonazepam, chlorazepate, clobazam, diazepam, halazepam, lorazepam, oxazepam and prazepam), zolpidem, and barbiturates. In still other embodiments, the nicotinamide riboside chloride preparations and pharmaceutical compositions of the invention that increase the level of NAD and/or the activity of a sirtuin protein may be used as part of a treatment with a 5-HT1A receptor partial agonist, such as selected from the group consisting of buspirone, flesinoxan, gepirone and ipsapirone. Nicotinamide riboside chloride preparations and pharmaceutical compositions of the invention that increase the level of NAD and/or the activity of a sirtuin protein can also used as part of a treatment with a norepinephrine reuptake inhibitor, such as selected from tertiary amine tricyclics and secondary amine tricyclics. Exemplary tertiary amine tricyclics include amitriptyline, clomipramine, doxepin, imipramine and trimipramine. Exemplary secondary amine tricyclics include amoxapine, desipramine, maprotiline, nortriptyline and protriptyline. In certain embodiments, nicotinamide riboside chloride preparations and pharmaceutical compositions of the invention that increase the level of NAD and/or activity of a sirtuin protein may be used as part of a treatment with a monoamine oxidase inhibitor, such as selected from the group consisting of isocarboxazid, phenelzine, tranylcypromine, selegiline and moclobemide.

In still another representative embodiment, nicotinamide riboside chloride preparations and pharmaceutical compositions of the invention that increase the level of NAD and/or the activity of a sirtuin protein may be used to reduce flushing side effects of chemotherapeutic agents, such as cyclophosphamide, and tamoxifen.

In another embodiment, nicotinamide riboside chloride preparations and pharmaceutical compositions of the invention that increase the level of NAD and/or the activity of a sirtuin protein may be used to reduce flushing side effects of calcium channel blockers, such as amlodipine.

In another embodiment, nicotinamide riboside chloride preparations and pharmaceutical compositions of the invention that increase the level of NAD and/or the activity of a sirtuin protein may be used to reduce flushing side effects of antibiotics. For example, nicotinamide riboside chloride preparations and pharmaceutical compositions of the invention that increase the level of NAD and/or the activity of a sirtuin protein can be used in combination with levofloxacin. Levofloxacin is used to treat infections of the sinuses, skin, lungs, ears, airways, bones, and joints caused by susceptible bacteria. Levofloxacin also is frequently used to treat urinary infections, including those resistant to other antibiotics, as well as prostatitis. Levofloxacin is effective in treating infectious diarrheas caused by *E. coli*, campylobacter jejuni, and shigella bacteria. Levofloxacin also can be used to treat various obstetric infections, including mastitis.

Other Uses

Nicotinamide riboside chloride preparations and pharmaceutical compositions of the invention that increase the level of NAD and/or the activity of a sirtuin protein may be used for treating or preventing viral infections (such as infections by influenza, herpes or papilloma virus) or as antifungal agents. In certain embodiments, nicotinamide riboside chloride preparations and pharmaceutical compositions of the invention that increase the level of NAD and/or the activity of a sirtuin protein may be administered as part of a combination drug therapy with another therapeutic agent for the treatment of viral diseases, including, for example, acyclovir, ganciclovir and zidovudine. In another embodiment, nicotinamide riboside chloride preparations and pharmaceutical compositions of the invention that increase the level of NAD and/or the activity of a sirtuin protein may be administered as part of a combination drug therapy with another anti-fungal agent including, for example, topical anti-fungals such as ciclopirox, clotrimazole, econazole, miconazole, nystatin, oxiconazole, terconazole, and tolnaftate, or systemic anti-fungal such as fluconazole (Diflucan), itraconazole (Sporanox), ketoconazole (Nizoral), and miconazole (Monistat I.V.).

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, nicotinamide riboside chloride preparations and pharmaceutical compositions of the invention may be administered to farm animals to improve their ability to withstand farming conditions longer.

Nicotinamide riboside chloride preparations and pharmaceutical compositions of the invention that increase the level of NAD and/or the activity of a sirtuin protein may also be used to increase lifespan, stress resistance, and resistance to apoptosis in plants. In one embodiment, a nicotinamide riboside chloride preparation or composition of the invention is applied to plants, e.g., on a periodic basis, or to fungi. In another embodiment, plants are genetically modified to produce a compound. In another embodiment, plants and fruits are treated with a nicotinamide riboside chloride preparation or composition of the invention prior to picking and shipping to increase resistance to damage during shipping. Plant seeds may also be contacted with a nicotinamide riboside chloride preparation or composition described herein, e.g., to preserve them.

In other embodiments, a nicotinamide riboside chloride preparation or composition of the invention that increase the level of NAD and/or the activity of a sirtuin protein may be used for modulating lifespan in yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

Nicotinamide riboside chloride preparations or compositions of the invention that increase the level of NAD and/or activity of a sirtuin protein may also be used to increase lifespan, stress resistance and resistance to apoptosis in insects. In this embodiment, a nicotinamide riboside chloride preparation or composition of the invention would be applied to useful insects, e.g., bees and other insects that are involved in pollination of plants. In a specific embodiment, a nicotinamide riboside chloride preparation or composition of the invention would be applied to bees involved in the production of honey. Generally, the methods described herein may be applied to any organism, e.g., eukaryote, that may have commercial importance. For example, they can be applied to fish (aquaculture) and birds (e.g., chicken and fowl).

Higher doses of a nicotinamide riboside chloride preparation or composition of the invention that increase the level of NAD and/or the activity of a sirtuin protein may also be used as a pesticide by interfering with the regulation of silenced genes and the regulation of apoptosis during development. In this embodiment, a nicotinamide riboside chloride preparation or composition of the invention may be applied to plants using a method known in the art that ensures the compound is bio-available to insect larvae, and not to plants.

At least in view of the link between reproduction and longevity (Longo and Finch, Science, 2002), nicotinamide riboside chloride preparations and compositions of the invention that increase the level of NAD and/or the activity of a sirtuin protein can be applied to affect the reproduction of organisms such as insects, animals and microorganisms.

EXEMPLIFICATION

The invention now being generally described, it will be more readily understood by reference to the following examples which are included merely for purposes of illustration of certain aspects and embodiments of the present invention, and are not intended to limit the invention in any way.

Example 1: Preparation of Anomerically Pure Nicotinamide Riboside Triacetate Trifluoromethanesulfonate

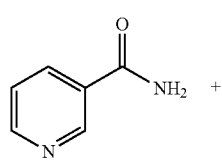

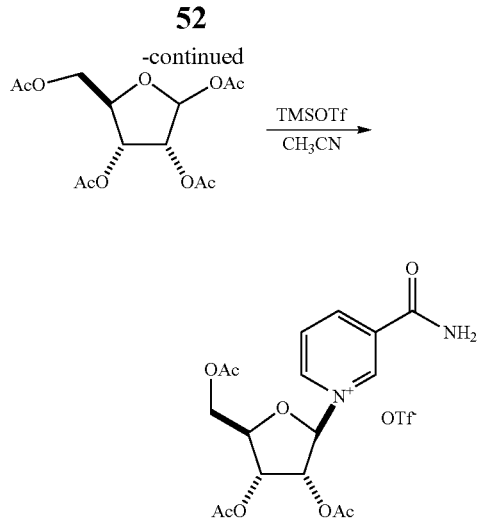

A 20 L reactor was charged with 576 g (4.71 mol) of nicotinamide (Aldrich or other commercial source) and 7.5 L of $CH_3CN$. To the stirred suspension was added 1.57 L (8.64 mol) of trimethylsilyl trifluoromethanesulfonate (TMSOTf) (Oakwood or other commercial source), all in one portion. The mixture was stirred until all of the nicotinamide had dissolved, then a solution of 500 g (1.57 mmol) of α/β-D-ribofuranose 1,2,3,5-tetraacetate (Zhang, P.; Dong, Z. E.; Cleary, T. P. Org. Proc. Res. Dev. 2005, 9, 583-592) in 1.25 L of $CH_3CN$ was added, all in one portion. The ribose ester remaining in the addition vessel was dissolved in 250 mL of $CH_3CN$, and this solution was added to the reaction. The reaction was stirred at ambient temperature for 30 min, during which time a white precipitate (comprising nicotinamide trifluoromethane-sulfonic acid salt) formed. Following the 30 minute reaction time, hydrolysis of the excess TMSOTf was begun by the addition of 50 mL of 1.2 M $NaHCO_{3(aq)}$, allowing gas evolution to ensue, then subside. An additional 425 g (5.06 mol) of $NaHCO_{3(s)}$ was added in portions to control gas evolution. After all of the $NaHCO_3$ was added, the suspension was stirred for 15 minutes. At this time, the reaction pH was 3. The solids were filtered, and the filter cake was washed with $CH_3CN$ (3×500 mL). The combined filtrate and washings solution was concentrated in vacuo to remove 8.5 L of solvent. For convenience, concentration could be interrupted, and the remaining solution could be stored at −20° C. for up to 18 h. The remaining solution was transferred back to the 20 L reactor, using 250 mL of methanol to rinse the last traces of reaction concentrate into the reactor. This solution was diluted with 5 L of $CH_2Cl_2$ to give a white precipitate consisting mainly of sodium trifluoromethanesulfonate (NaOTf) and nicotinamide trifluoromethanesulfonic acid salt. The mixture was filtered, and the filter cake was washed with 2 L of $CH_2Cl_2$. The combined filtrate and washings solution was concentrated in vacuo to a thick oil. (For convenience, concentration could be interrupted, and the remaining solution could be stored at −20° C. for up to 18 h.) After $CH_2Cl_2$ distillation had slowed to a trace, the remaining oil was taken up in 1 L of methanol, and then the solution was concentrated in vacuo to remove any remaining $CH_2Cl_2$.

Example 2: Preparation of Nicotinamide Riboside Chloride by Ion Exchange from Nicotinamide Riboside Trifluoromethane Sulfonate and Acetate to Chloride

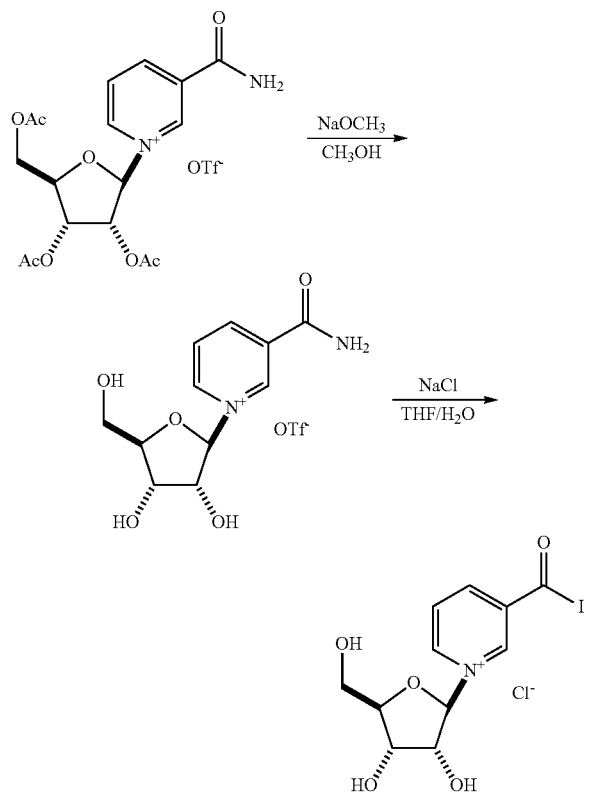

The residue was transferred back into the 20 L reactor with 7.5 L of methanol. An ice bath was applied to the reactor to adjust the internal temperature to 3° C. Separately, 3.75 L (3.75 mol) of 1M NaOCH₃ in methanol was cooled to 3° C., then this solution was added to the reactor over 10 minutes. The internal temperature was maintained below 5° C. during the addition. After addition was complete, the reaction was stirred for 30 min, then 1.25 L (3.75 mol) of 3M HCl was added slowly, keeping the internal temperature below 5° C. At the end of the HCl addition the pH=3. The solvent was removed in vacuo. (For convenience, the partially concentrated solution could be stored at 4° C. for up to 48 h. After concentration was complete, the residue could be stored at -20° C. for up to 18 h. To remove the residual methanol, the evaporation residue was dissolved in water and concentrated in vacuo (3×1 L). The residue was taken up in 5 L of water, and adjusted to pH=4 with 2M NaOH$_{(aq)}$. Sodium chloride (NaCl) was added to the solution, and the mixture was stirred at ambient temperature until saturated with NaCl, leaving about 5 g of undissolved NaCl. The saturated solution was extracted with tetrahydrofuran (THF, 3×5 L). The aqueous layer was monitored by ¹H NMR to confirm that acetic acid was removed after the extractions were complete.

The aqueous phase was adjusted to pH=6-7 with 2M NaOH$_{(aq)}$, then extracted with THF (4×5 L). The aqueous layer was monitored by ¹H NMR to confirm that the residual nicotinamide was <5 mol % relative to nicotinamide riboside. ¹⁹F NMR was also used to confirm the absence of trifluoromethanesulfonate in the aqueous layer. The aqueous layer was then concentrated in vacuo to remove 2.5 L of water. The remaining suspension was diluted with 5 L of ethanol, filtered, and the salt precipitate was washed with 2.5 L of ethanol. The combined filtrate and washings solution was concentrated in vacuo to a thick oil. This was stirred with 1.5 L of methanol, the precipitate was filtered, and the solution was concentrated in vacuo. The residue was stirred with another 1.5 L of methanol, the precipitate was filtered, and the solution was concentrated in vacuo. The residue was stirred with a third 1.5 L portion of methanol, the precipitate was filtered, and the solution was concentrated in vacuo to give 385 g of a red-orange oil. The amount of residual methanol was determined to be 34 g by ¹H NMR, for a crude yield of 351 g (77%).

The THF extractions served to remove most of the excess nicotinamide. Because sodium trifluoromethanesulfonate is soluble in THF, the extractions also removed sodium trifluoromethanesulfonate from the solution, while leaving nicotinamide riboside in the aqueous layer with a chloride counterion. This allowed for the preparation of anomerically pure nicotinamide riboside chloride, in contrast to previous syntheses of nicotinamide riboside chloride, which delivered anomeric mixtures of nicotinamide riboside chloride (Jarman, M. Ross, W. C. J. *J. Chem. Soc.* (C) 1969, 199-203; Haynes, L. J.; Hughes, N. A.; Kenner, G. W.; Todd, A. *J. Chem. Soc.* 1957, 3727-3732). More recent syntheses of nicotinamide riboside have delivered anomerically pure material as either the bromide, trifluoromethanesulfonate or trifluoroacetate salts, which are less desirable for human consumption than the chloride.

Figure 3:
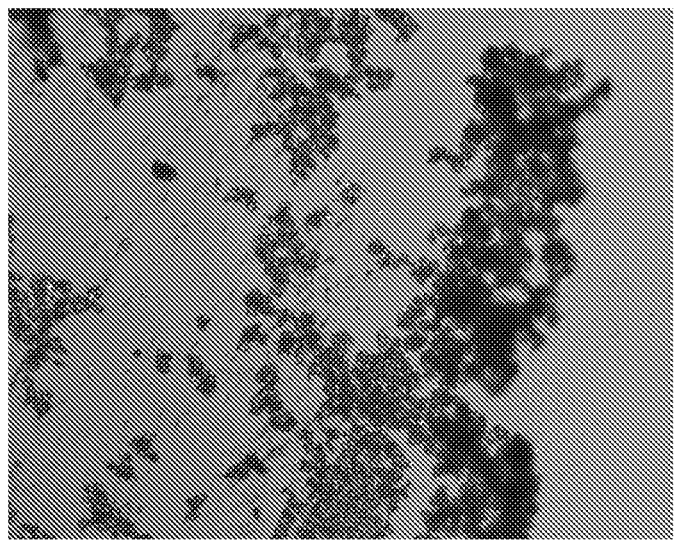
FIG. 3 is a photograph of nicotinamide riboside chloride-0.9 methanol salt crystals at 90× magnification under plane polarized light.

Example 3: Preparation of Nicotinamide Riboside Chloride ●0.9 Methanol Crystals Crude product (351 g) from the above example was dissolved in 1.5 L of methanol, then 625 mL of methanol was removed in vacuo. For the initial crystallization experiments, this solution was placed in a glass round-bottomed flask, and the side was scratched with a metal spatula. The solution was then stored at -20° C. for several weeks until a crystalline precipitate formed. The crystalline solid differed from the amorphous solid in that it could be filtered under ambient conditions while remaining free-flowing. In contrast, the amorphous solid formed an amber, sticky mass on the filter upon exposure to ambient humidity. For subsequent preparations, the methanol solution was seeded with 100 mg of crystalline nicotinamide riboside chloride, and the solution was allowed to stand at ambient temperature while the product crystallized over the course of several hours. Using a Buchner funnel filtration apparatus, the crystals were filtered and washed with 200 mL of ice-cold methanol. The product was dried on the filter, open to the air, for 1.5 h, then under high vacuum (<1.0 mM Hg) at ambient temperature for 18 h. The yield was 157 g (34%) of a light yellow solid. The product contained 0.9 molar equivalents of methanol by ¹H NMR integration (i.e., nicotinamide riboside chloride ●0.9 methanol crystals). This residual methanol could not be removed by additional drying at <40° C. The resulting product was an anhydrous crystalline form of the biologically active form of nicotinamide riboside chloride (i.e., 3-carbamoyl-1-((2R,3R,4S,5R)-3,4-dihydroxy-5-(hydroxymethyl)tetrahydrofuran-2-yl)pyridin-1-ium chloride). ¹H NMR (300 MHz, D₂O), data were identical to those reported for the form isolated from ethanol, with an additional resonance at 3.30 ppm corresponding to 0.9 equivalent of $CH_3OH$. IR ($cm^{-1}$) 3361, 1674, 1610, 1394, 1082, 982, 833, 792 (The IR plot is included as FIG. 7). The crystalline nature of this product was confirmed by optical microscopy using polarized light (FIG. 3). X-ray powder diffraction data are included as FIG. 4 (XRPD (degrees) −11.1, −7.1, −2.9, 1.0, 4.7, 15.2, 18.2, 21.4, 23.5, 24.9, 26.0, 27.7).

Example 4: Preparation of Nicotinamide Riboside Chloride Crystals Containing <5000 ppm Ethanol To prepare the first batch of crystals for use as seed to subsequent scale-up batches, 100 mg of nicotinamide riboside chloride containing 0.9 molar equivalent of methanol was dissolved in 5 mL of methanol, and then the solution was diluted with 10 mL of ethanol. The solution was concentrated in vacuo to a volume of 5 mL, then 5 mL of ethanol was added. The solution was concentrated in vacuo a second time to a volume of 5 mL, and then another 5 mL of ethanol was added. The solution was concentrated in vacuo a third time to a volume of 5 mL, then 5-10 mg of nicotinamide riboside chloride crystals containing 0.9 molar equivalent of methanol was added, but no crystallization ensued. The mixture was concentrated to 3 mL to give an amorphous precipitate. A 2 mL portion of ethanol was added to this mixture to dissolve the precipitate, giving a solution. The flask was capped with a rubber septum and allowed to stand at ambient temperature for 4 days. The solvent was decanted from the crystals, and then these crystals were dried in vacuo to give 15 mg of light tan hemispheres. This material was used to seed the immediately subsequent crystallizations.

A 75 g portion of crystalline nicotinamide riboside chloride containing 0.9 molar equivalent methanol was dissolved in 100 mL of water. This solution was diluted with 2.0 L of ethanol with swirling, then it was allowed to stand for 5 min at ambient temperature. Next, the solution was seeded with 50 mg of anhydrous nicotinamide riboside chloride crystals. The mixture was allowed to stand for 15 h at ambient temperature, then the crystalline product was filtered using a Buchner funnel, washed with 100 mL of ethanol, then dried on the filter, with continued suction and open to the air, for 1.5 h to give 43.2 g of light tan crystals. The supernatant was concentrated in vacuo at 40° C. to 500 mL, and then the resulting suspension was stirred for 2.25 h at ambient temperature. The precipitate was filtered, washed with 100 mL of ethanol, and then dried on the filter to give 12.8 g of additional product. The total yield was 56 g of nicotinamide riboside chloride.

Figure 5:
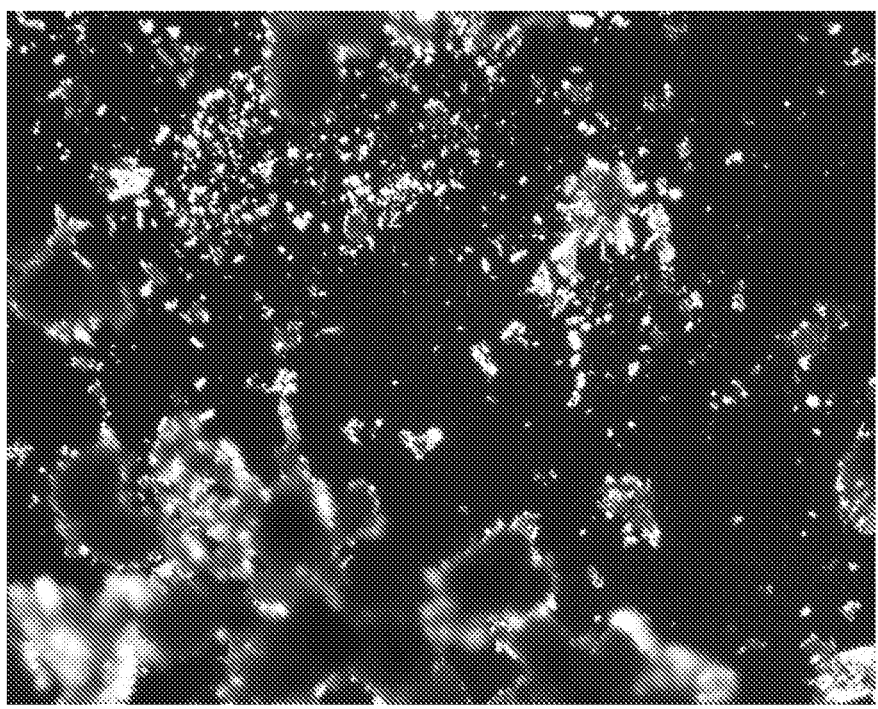
FIG. 5 is a photograph of nicotinamide riboside chloride salt crystals at 90× magnification under plane polarized light.
Figure 8:
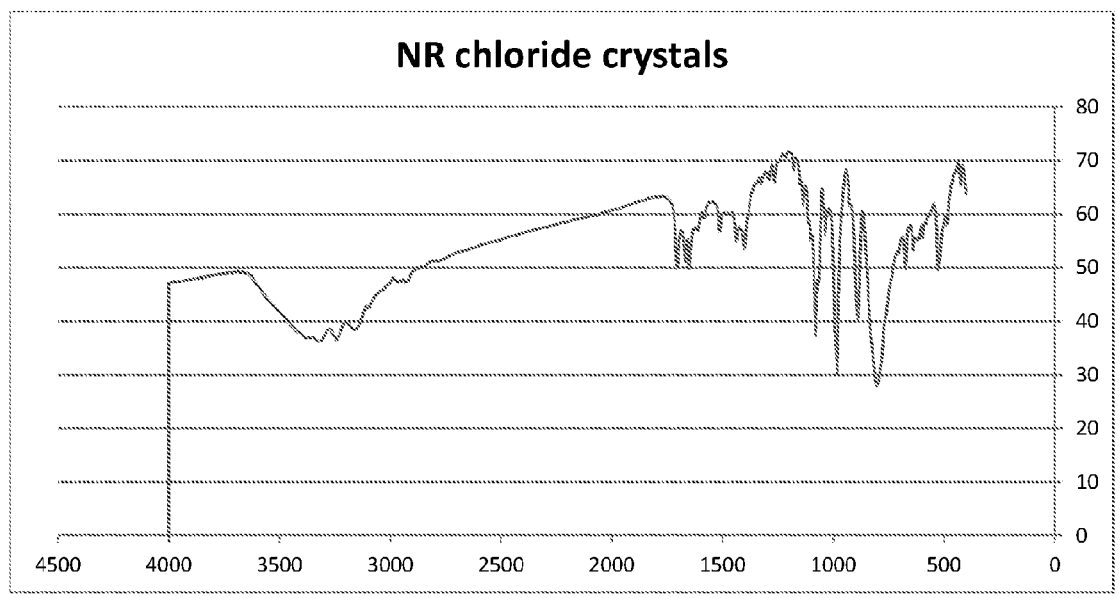
FIG. 8 is an infrared absorption spectrum of crystalline nicotinamide riboside, crystallized from ethanol solution.
Figure 9:
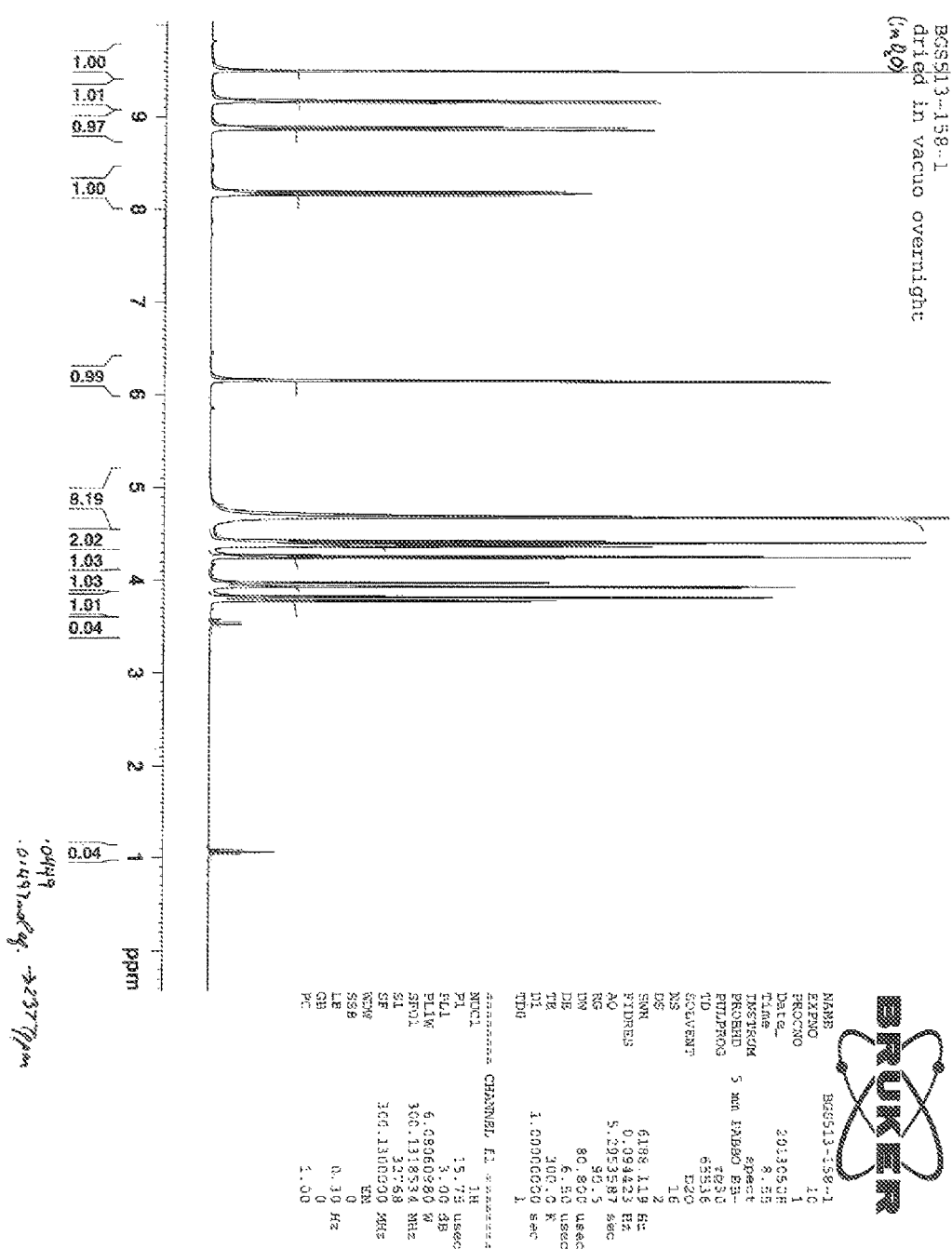
FIG. 9 is a $^1$H NMR spectrum in $D_2O$ of nicotinamide riboside chloride crystallized from ethanol.
Figure 10:
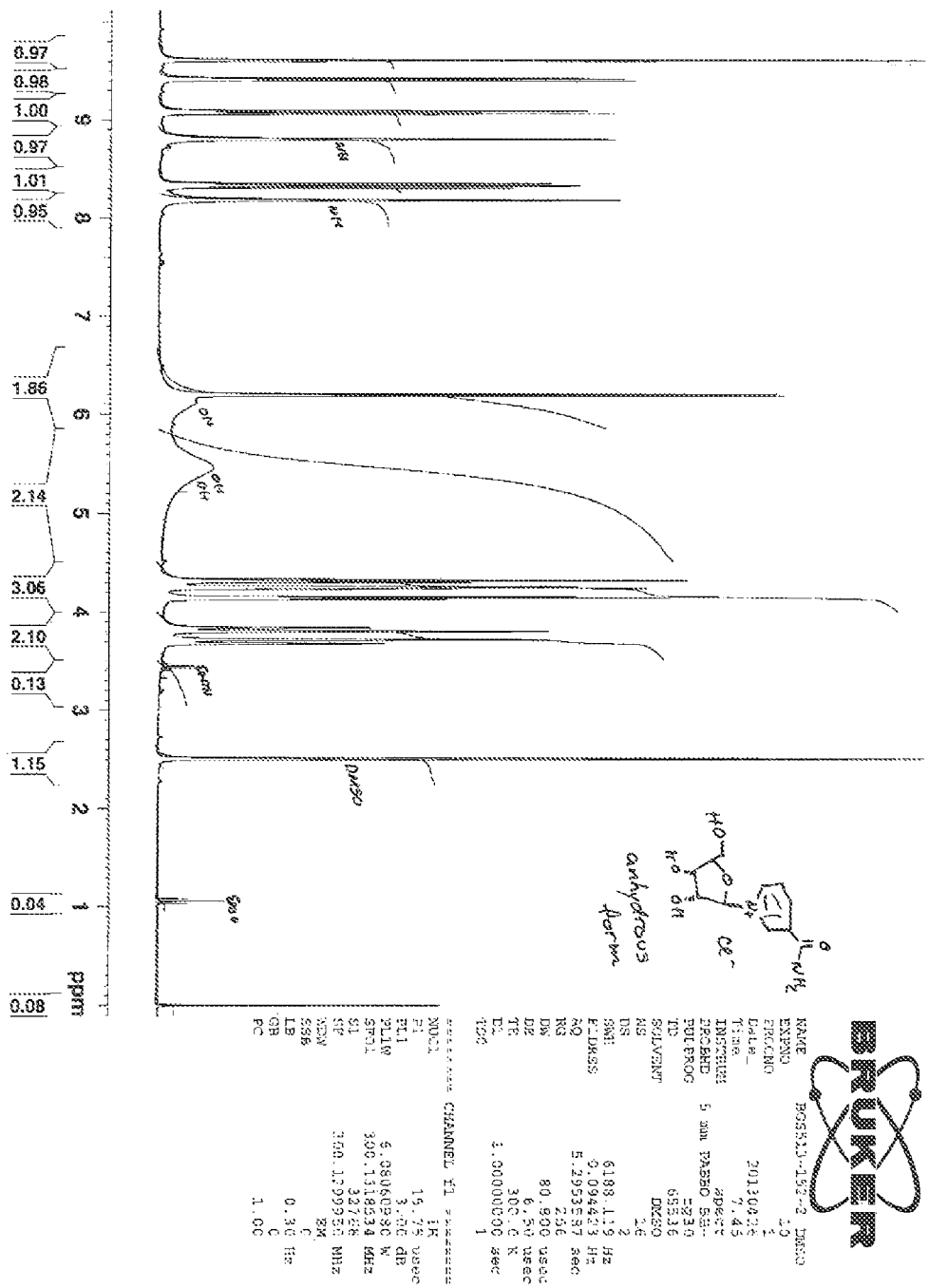
FIG. 10 is a $^1$H NMR spectrum of nicotinamide riboside chloride in $d_6$-DMSO (deuterated DMSO having the chemical formula $((CD_3)_2S=O)$.
Figure 11:
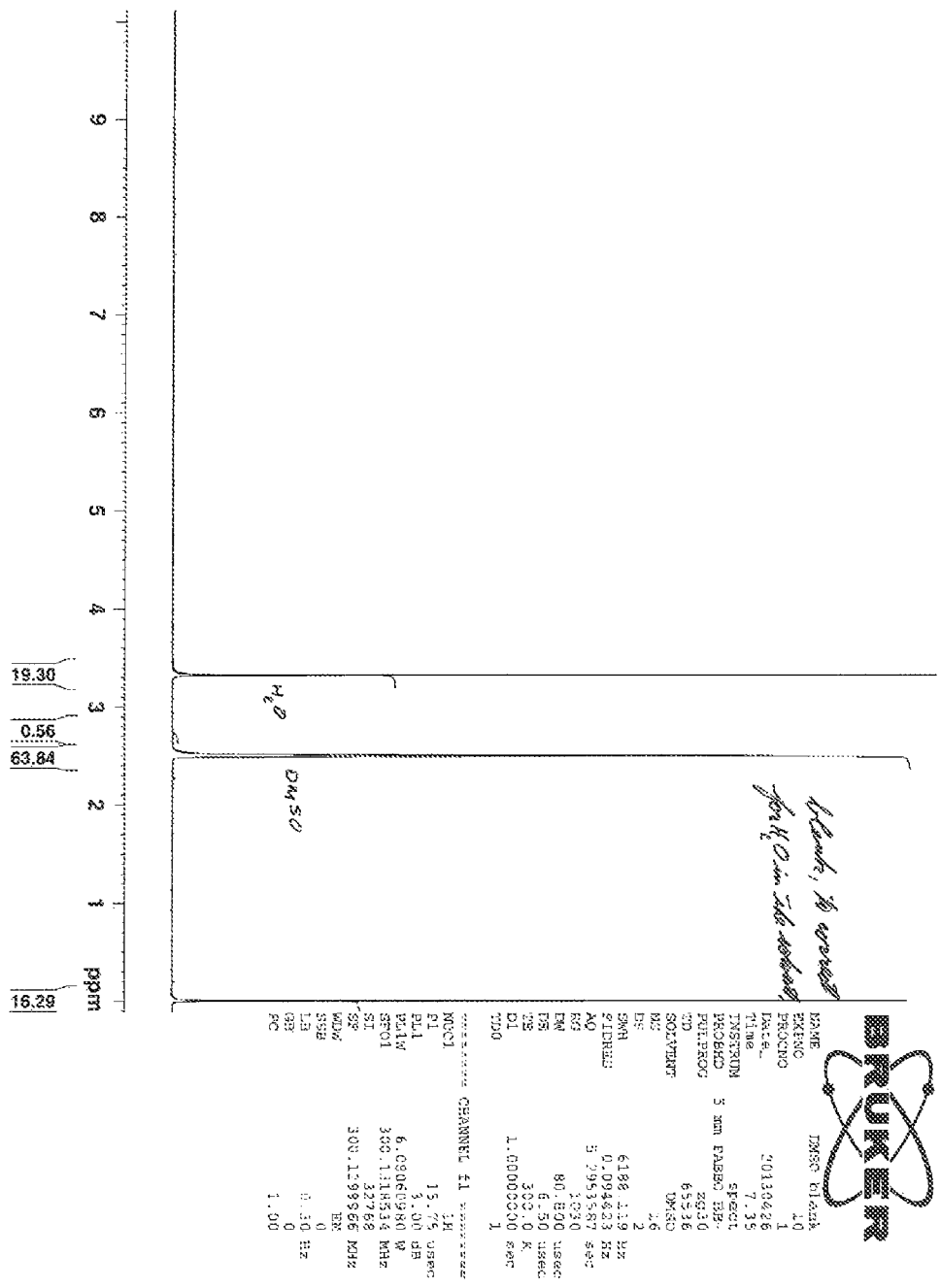
FIG. 11 is a $^1$H NMR spectrum of the solvent for the $^1$H NMR spectrum of nicotinamide riboside in $d_6$-DMSO shown in FIG. 10.
Figure 12:
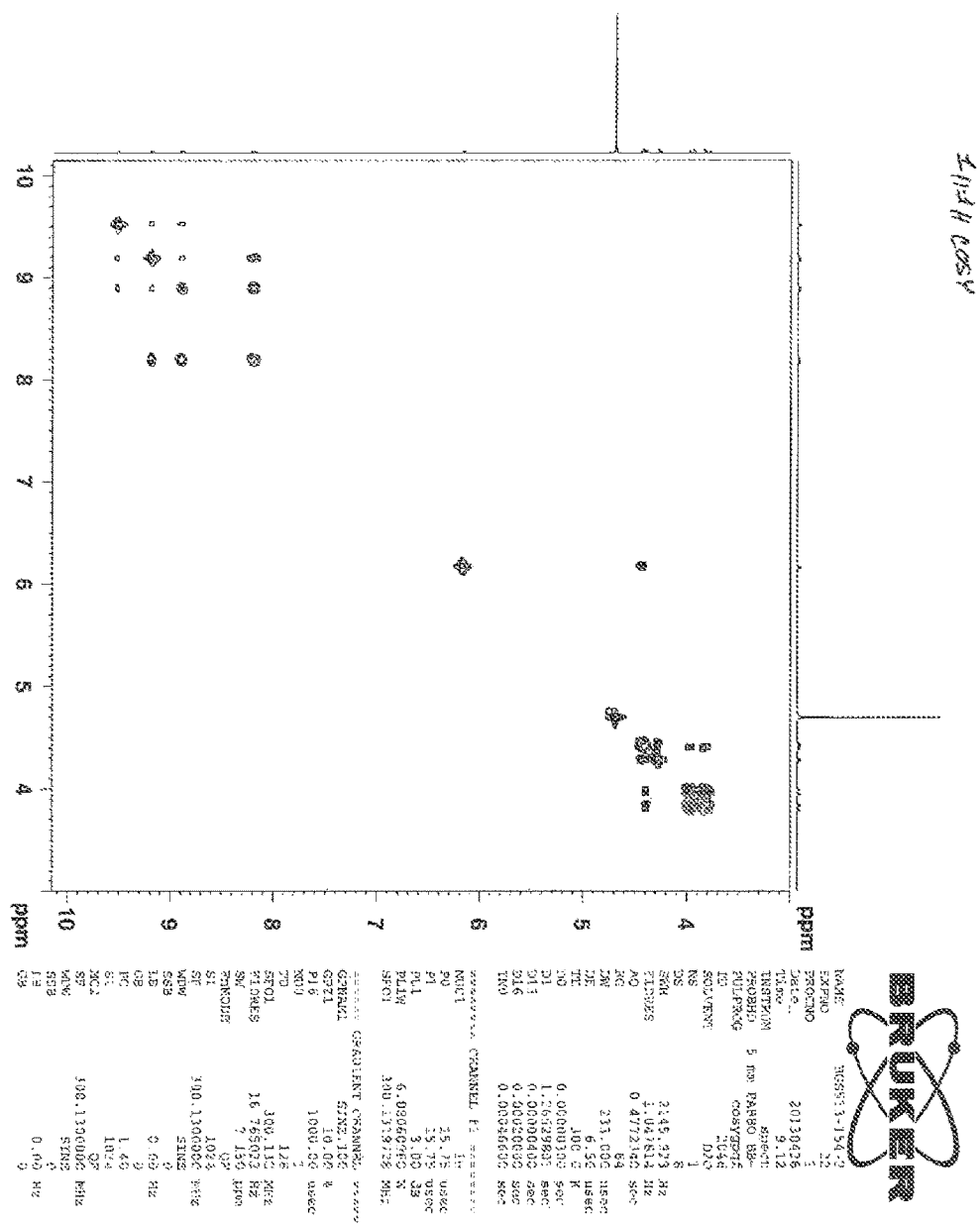
FIG. 12 is a COSY (Correlation Spectroscopy) NMR spectrum of nicotinamide riboside evidencing purity and identity.
Figure 13:
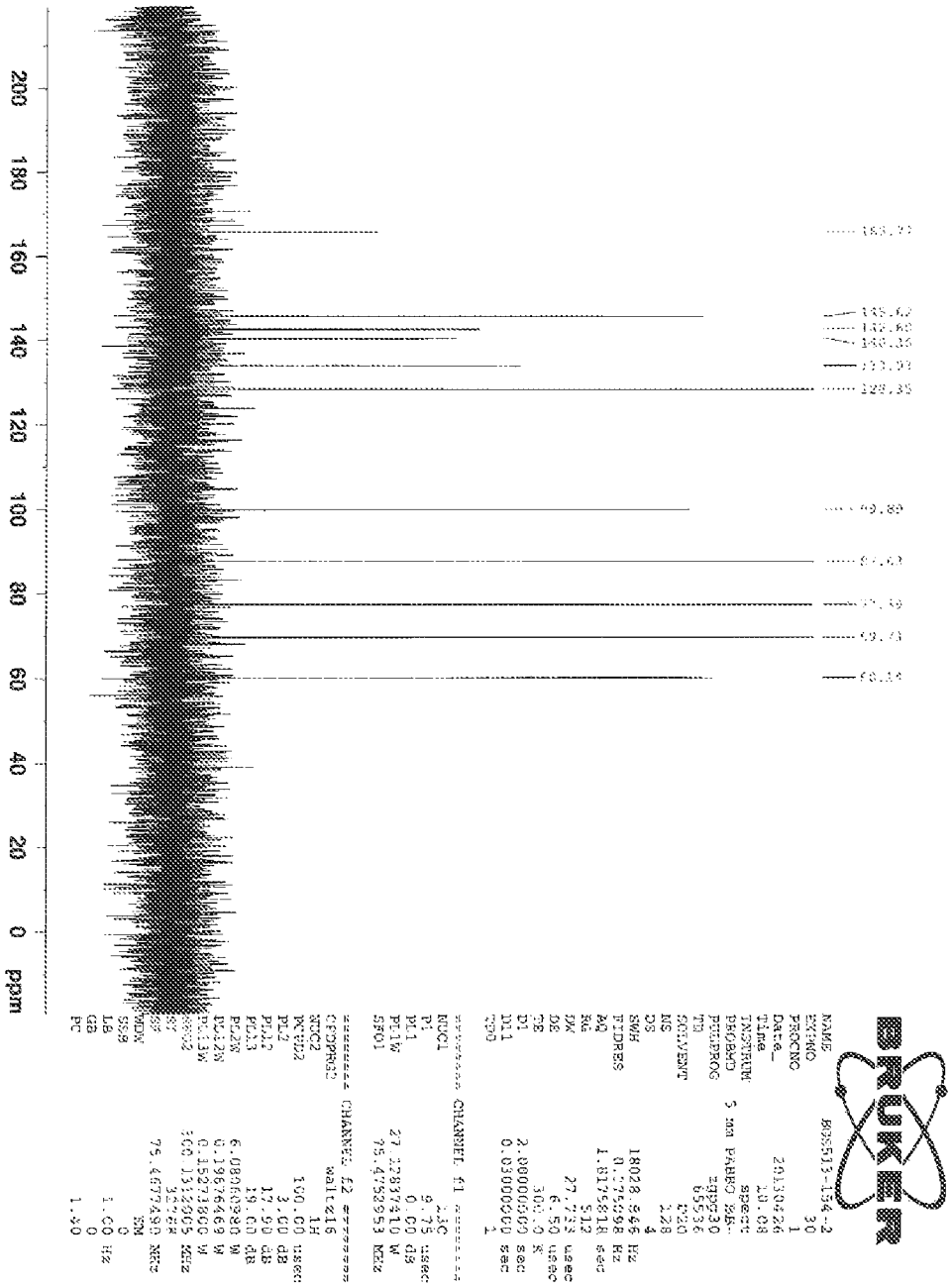
FIG. 13 is a $^{13}$C NMR spectrum of nicotinamide riboside.
Figure 14:
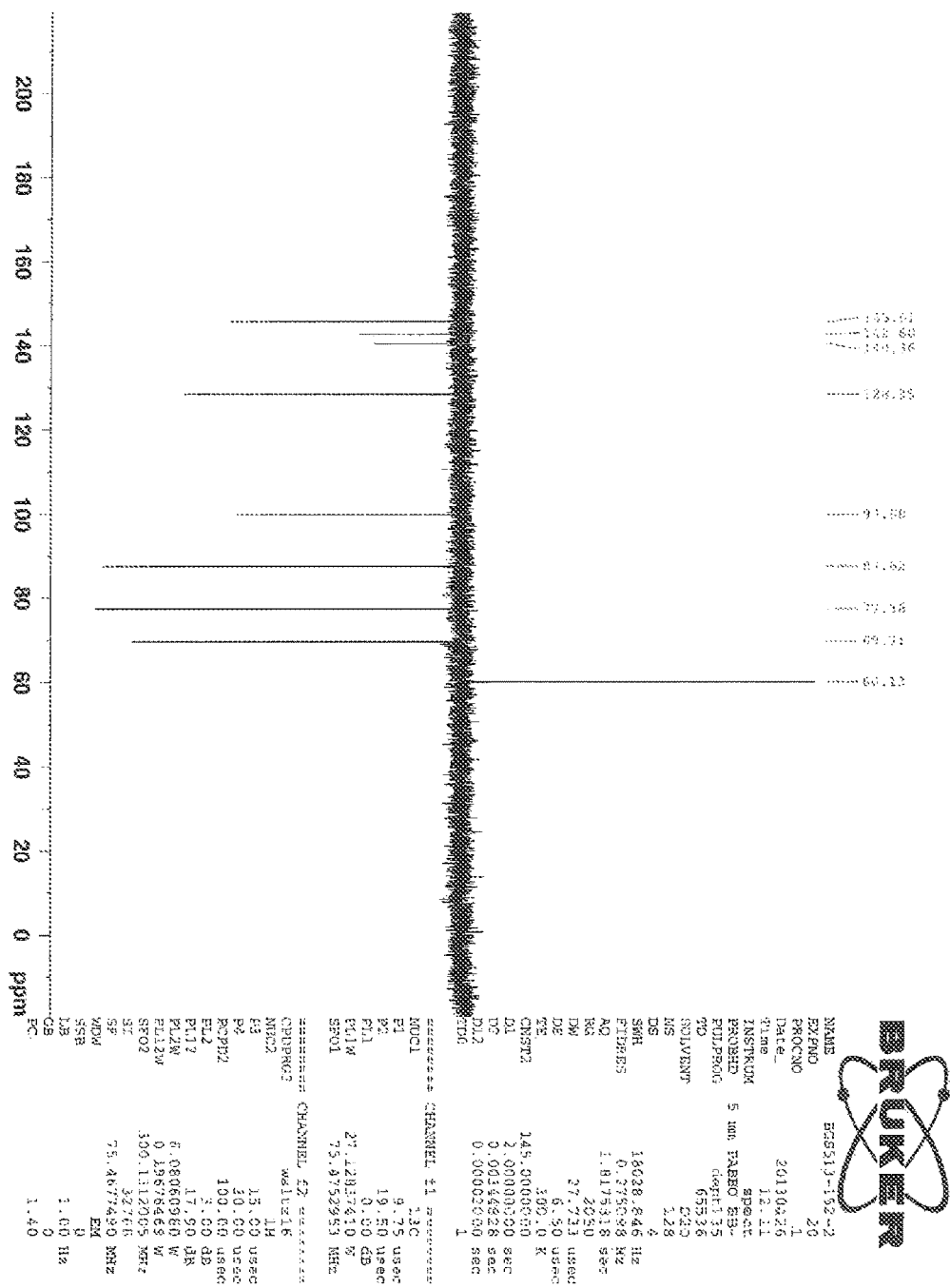
FIG. 14 is a DEPT135 (Distortionless Enhancement by Polarization Transfer) NMR spectrum of nicotinamide riboside showing proton (—H) positioning.
Figure 15:
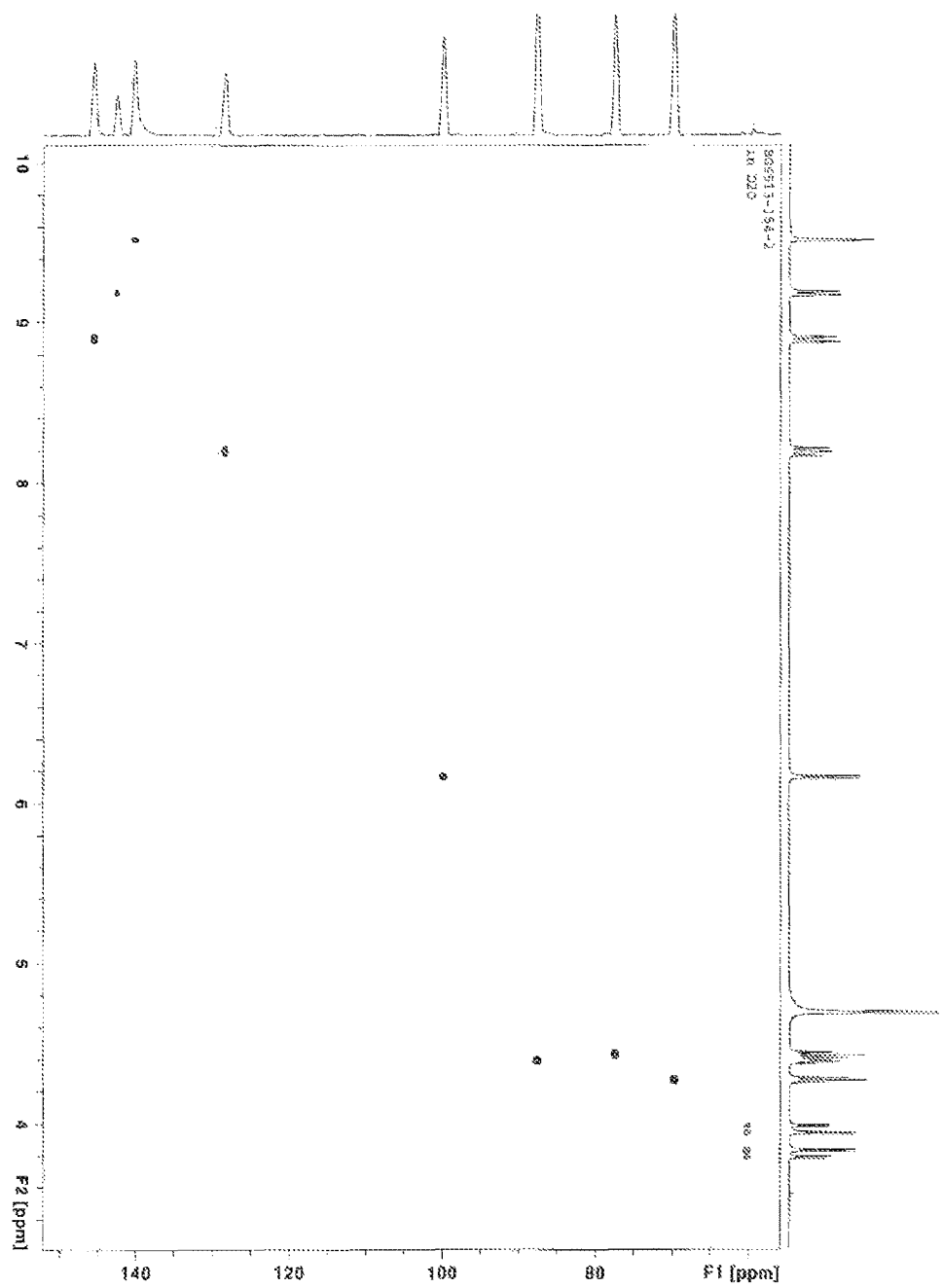
FIG. 15 is a HSQC (Heteronuclear Single Quantum Coherence) NMR spectrum of nicotinamide riboside in $D_2O$ solution showing carbon-proton couplings.

$^1H$ NMR analysis in $D_2O$ solution showed that this product contained no methanol, and <5000 parts per million of residual ethanol (FIG. 9). $^1H$ NMR analysis ($d_6$-DMSO) showed that these crystals were anhydrous (FIG. 10). The crystalline nature of this product was confirmed by optical microscopy using polarized light (FIG. 5). A 50 mg portion of this material was dried under high vacuum (<1.0 mm Hg) and at ambient temperature for 48 h. The crystals did not show a well-defined melting point. The material completely decomposed, without melting, within 17 min at 100° C. at <1 mm Hg. (Decomposition was confirmed by $^1H$ NMR spectral analysis in $D_2O$ solution after the heating period.) In contrast, a sample could be heated at 80° C. for 1 h and <1 mm Hg with <3% decomposition. $^1H$ NMR (400 MHz, $D_2O$) δ 9.63 (s, 1H, H2), 9.31 (d, 1H, J=5.9 Hz, H4), 9.01 (dd, 1H, J=8.0 Hz, 1.0 Hz, H6), 8.32 (dd, 1H, J=8.0 Hz, 5.9 Hz, H5), 6.29 (d, 1H, J=3.9 Hz, H1'), 4.55 (t, 1H, J=3.9 Hz, H2'), 4.50 (m, 1H, H4'), 4.38 (t, 1H, J=3.9 Hz, H3'), 4.08 (dd, 1H, J=12, 3 Hz, H5'), 3.93 (dd, 1H, J=12, 3, Hz, H5'); $^{13}C$ NMR (75 MHz, $D_2O$) δ 165.8 (C7), 145.6 (C6), 142.6 (C4), 140.4 (C2), 133.9 (C3), 128.4 (C5), 99.9 (C1'), 87.6 (C4'), 77.4 (C2'), 69.7 (C3'), 60.1 (C5'); IR (cm−1) 3299, 1700, 1398, 1080, 982, 887, 795 (see FIG. 8). XRPD (degrees) 14.2, 17.1, 20.5, 22.7, 23.8, 25.1, 26.8, 34.2 X-ray powder diffraction (XRPD) data are included as FIG. 6. The XRPD serves as a fingerprint for the crystalline form of nicotinamide riboside chloride with only trace residual solvents present.

Example 5: NR Chloride Increases NAD in Dermal Fibroblasts

Human primary dermal fibroblasts derived from adult human skins (HDFa, Life technologies, Grand Island, NY, Passage 2-4) were grown in Medium 106 (Life Technologies) supplemented with Low Serum Growth Supplement (LSGS) (Life Technologies) and seeded in 12-well plates with density at 2×105 cells per well and 1 ml of culture medium in each well.

Stock solution of NR chloride (MW: 322.742, GSK3002633B) was prepared freshly in water at 100 mM. Cells were treated with NR chloride at different concentrations as shown in FIG. 5 for 6 and 24 hrs, washed twice with PBS containing 5 mM EDTA, and then subject to Nicotinamide adenine dinucleotide (NAD) measurement. In brief, acetonitrile (ACN) lysis buffer (Ammonium Acetate (50 mM) and 90% acetonitrile) was added to each well (200 μl/well) to lyse the cells at RT for 5-10 mins by gently rotating on a culture plate shaker at a low speed. Enzyme master mix (300 μM of 5-Amino-(3,4'-bipyridin)-6(1H)-one (Inamrinone) (Sigma-Aldrich), a substrate for ADP ribosyl cyclase (ADPR cyclase)) and 30 nM ADPR Cyclase (Sigma, St. Louis, Mont.), in 75 mM HEPES pH7 buffer (Life Technologies)) was added to the lysed cells (400 μl of enzyme master mix/well). Enzymatic reaction was incubated at RT for ~30 min. At the end of incubation, the supernatant (200 μl) of the reaction solution from each well was transferred to each well of a 96-well plate and absorbance was read twice in the 96-well plate at 405 nm using a plate reader (Spectra Maxplus, Molecular Devices, Sunnyvale, Calif.). A mixture of enzyme master mix and ACN extraction solution at 2:1 ratio was used as a blank reference.

Figure 16:
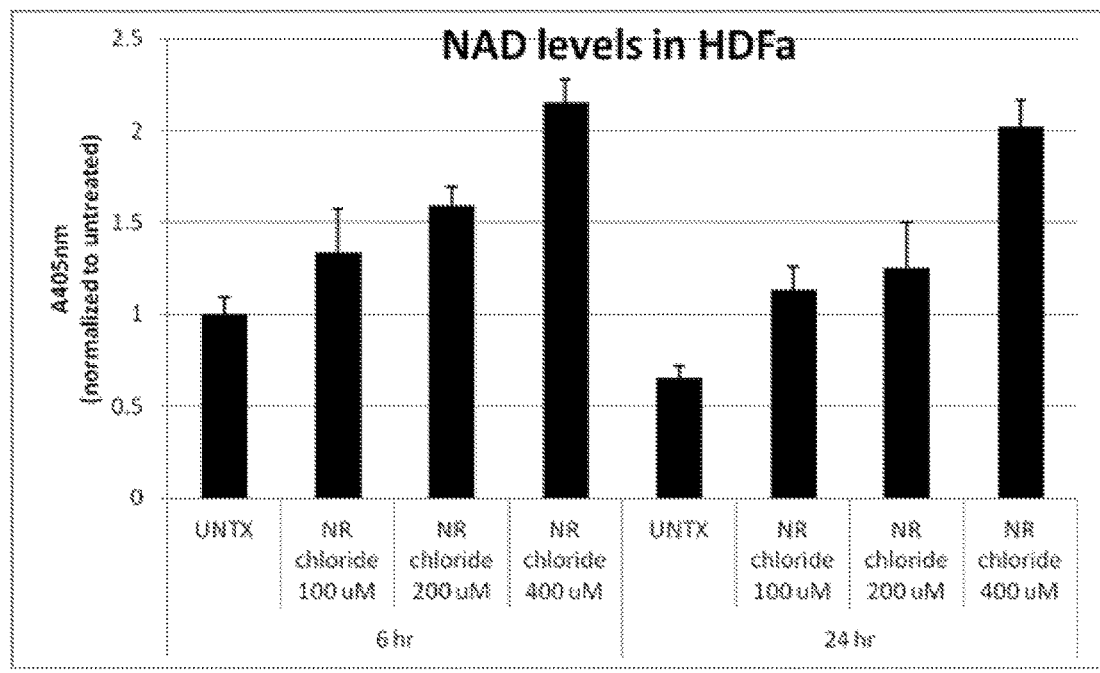
FIG. 16 is a bar graph showing that NR chloride dose-dependently increased NAD levels from dermal fibroblasts at both 6 and 24 hrs.

Isolated, chemically-pure NAD (Sigma) was used as a positive control. Other NAD assays are known in the art or otherwise publically available as a kit (see, e.g., Neubert, D., et al., *Biochim. Biophys. Acta*, 1964, 92, 610-12; Emanuelli, M., et al. *J. Chromatog. B*. 676, 13-18; and NAD/NADH Cell-Based Assay Kit by Cayman Chemical). The results shown in FIG. 16 demonstrate that NR chloride salt dose-dependently increases intracellular NAD levels in dermal fibroblasts.

EQUIVALENTS

The present invention provides among other things nicotinamide riboside NAD precursor compounds, and salts and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

Also incorporated by reference are the following: PCT Publications WO2005/002672; 2004/016726; WO 2006/086454; and WO 2006/105440.

What is claimed is:

1. A substantially isomerically pure 3-carbamoyl-1-((2R,3R,4S,5R)-3,4-dihydroxy-5-(hydroxymethyl)tetrahydrofuran-2-yl)pyridin-1-ium (β-D-nicotinamide riboside (or 2R (β) nicotinamide riboside)) chloride crystal of greater than 90% chemical purity (w/w) containing <5000 ppm ethanol and <1000 ppm other solvents.

2. A substantially isomerically pure 3-carbamoyl-1-((2R,3R,4S,5R)-3,4-dihydroxy-5-(hydroxymethyl)tetrahydrofuran-2-yl)pyridin-1-ium (β-D-nicotinamide riboside (or 2R (β) nicotinamide riboside)) chloride methanolate crystal of greater than 90% chemical purity (w/w) containing between 0.01 and 1.1 molar equivalent of methanol and <1000 ppm other solvents.

3. The substantially isomerically pure 3-carbamoyl-1-((2R,3R,4S,5R)-3,4-dihydroxy-5-(hydroxymethyl)tetrahydrofuran-2-yl)pyridin-1-ium (β-D-nicotinamide riboside) chloride methanolate crystal of claim 2 containing between 0.7 and 1.1 molar equivalent of methanol.

4. The substantially pure β-D-nicotinamide riboside (2R (β) nicotinamide riboside) chloride crystal of claim 1, comprising less than 1% (m/m) of 3-carbamoyl-1-((2S,3R,4S,5R)-3,4-dihydroxy-5 (hydroxymethyl)tetrahydrofuran-2-yl)pyridin-1-ium (2S (α) nicotinamide riboside) chloride.

5. The substantially isomerically pure β-D-nicotinamide riboside (2R (β) nicotinamide riboside) chloride crystal of claim 1 having a chemical purity of greater than 95% (w/w).

6. The substantially isomerically pure β-D-nicotinamide riboside (2R (β) nicotinamide riboside) chloride crystal of claim 1, having a chemical purity greater than or equal to 99% (w/w).

7. The substantially isomerically pure β-D-nicotinamide riboside (2R (β) nicotinamide riboside) chloride crystal of claim 1, containing <4000 ppm ethanol.

8. The substantially isomerically pure β-D-nicotinamide riboside (2R (β) nicotinamide riboside) chloride crystal of claim 1, containing a level of ethanol selected from the group consisting of 0-100 ppm ethanol, 100-200 ppm ethanol, 200-300 ppm ethanol, 300-400 ppm ethanol, and 400-500 ppm ethanol.

Figure 6:
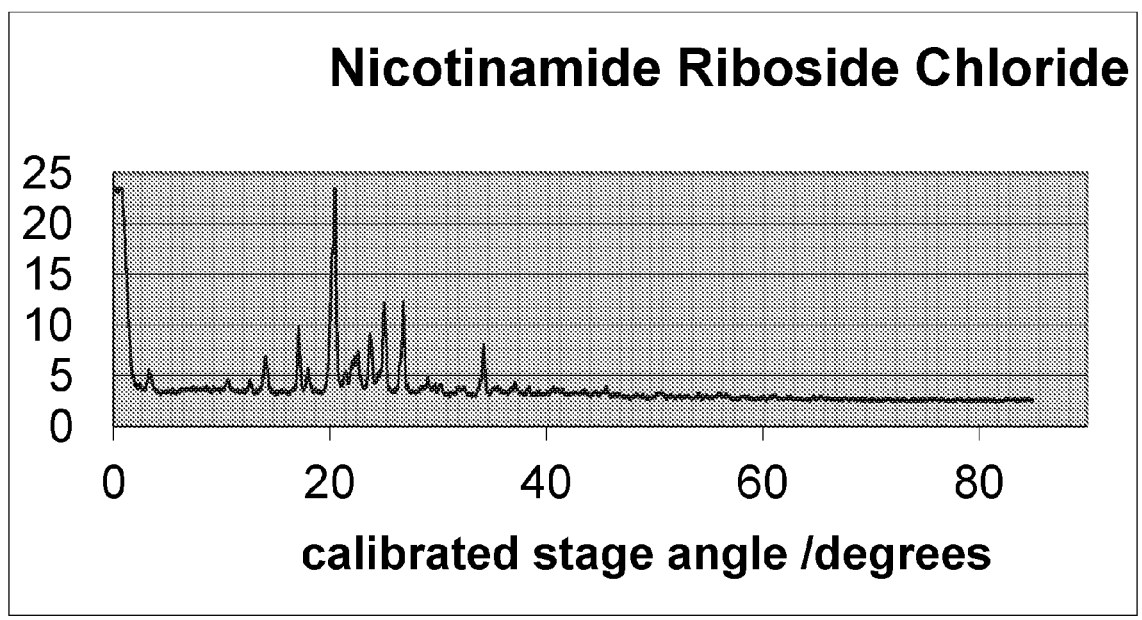
FIG. 6 is an X-ray powder diffraction pattern for nicotinamide riboside chloride crystals from ethanol, with <5000 ppm ethanol.

9. The substantially isomerically pure β-D-nicotinamide riboside (2R (β) nicotinamide riboside) chloride crystal of claim 1, having an X-ray powder diffraction pattern as shown in FIG. 6.

10. The substantially isomerically pure β-D-nicotinamide riboside (2R (β) nicotinamide riboside) chloride crystal of claim 1, having four or more of the following X-ray powder diffraction peaks: about 14.2, about 17.1, about 20.5, about 22.7, about 23.8, about 25.1, about 26.8, and about 34.2 degrees.

11. The substantially isomerically pure β-D-nicotinamide riboside (2R (β) nicotinamide riboside) chloride crystal of claim 1, having an infrared absorption spectrum as shown in FIG. 8.

12. The substantially isomerically pure β-D-nicotinamide riboside (2R (β) nicotinamide riboside) chloride crystal of claim 1, having an IR spectrum comprising peaks at (cm$^{-1}$) 3299, 1700, 1398, 1080, 982, 887, and 795.

Figure 4:
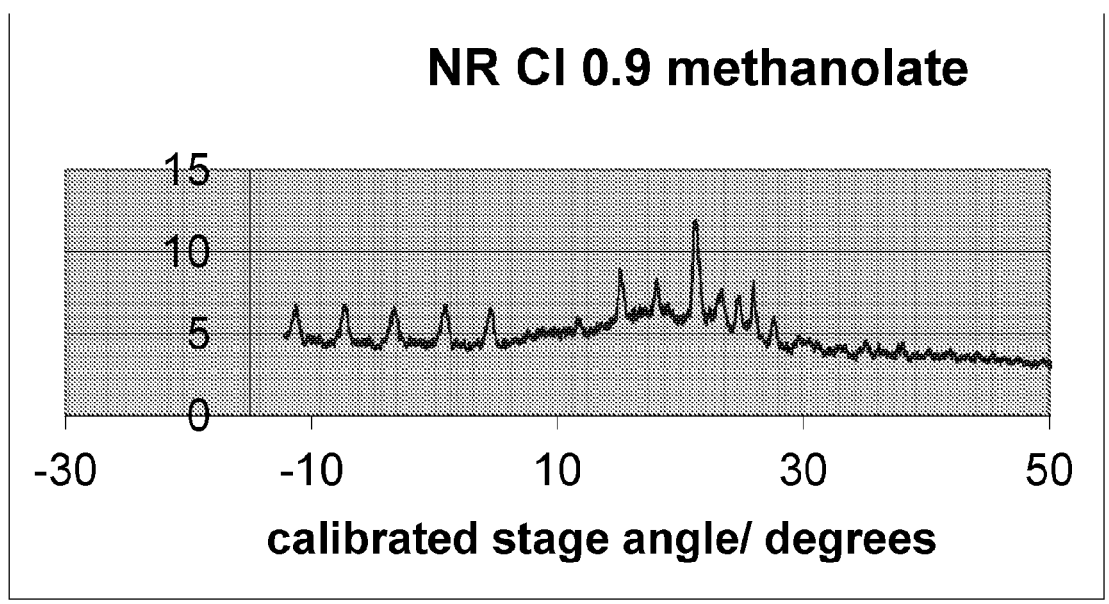
FIG. 4 is an X-ray powder diffraction pattern of nicotinamide riboside chloride methanolate salt crystals.

13. The substantially isomerically pure β-D-nicotinamide riboside (2R (β) nicotinamide riboside) chloride methanolate crystal of claim 2, having an X-ray powder diffraction pattern as shown in FIG. 4.

14. The substantially isomerically pure β-D-nicotinamide riboside (2R (β) nicotinamide riboside) chloride methanolate crystal of claim 2, having five or more of the following X-ray powder diffraction peaks (degrees): about −11.1, about −7.1, about −2.9, about 1.0, about 4.7, about 15.2, about 18.2, about 21.4, about 23.5, about 24.9, about 26.0, and about 27.7 degrees.

Figure 7:
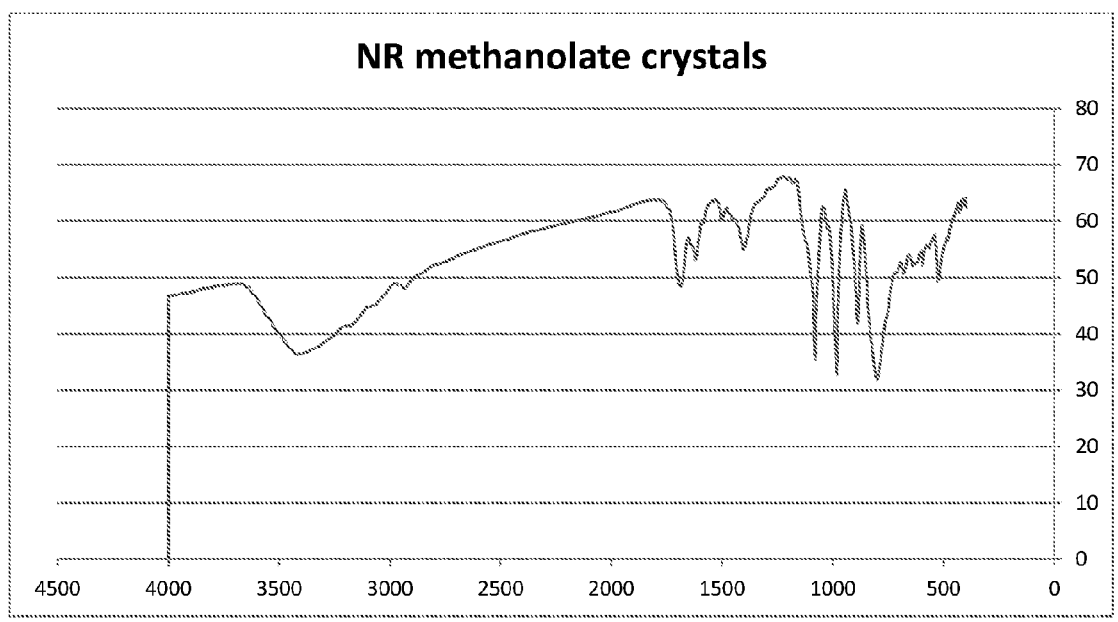
FIG. 7 is an infrared absorption spectrum of crystalline nicotinamide riboside methanolate, crystallized from methanol solution.

15. The substantially isomerically pure β-D-nicotinamide riboside (2R (β) nicotinamide riboside) methanolate crystal of claim 2, having an infrared absorption spectrum as shown in FIG. 7.

16. The substantially isomerically pure β-D-nicotinamide riboside (2R (β) nicotinamide riboside) methanolate crystal of claim 2, having an infrared absorption spectrum comprising peaks at (cm$^{-1}$) 3361, 1674, 1610, 1394, 1082, 982, 833, and 792.

17. A pharmaceutical composition comprising a β D-nicotinamide riboside (2R (β) nicotinamide riboside) chloride crystal of claim 1.

18. The pharmaceutical composition of claim 17, wherein the pharmaceutical composition is for intranasal, dermal, urogenital, ophthalmic, otologic, or respiratory inhalation administration.

19. A method of preparing an aqueous solution of 3-carbamoyl-1-((2R,3R,4S,5R)-3,4-dihydroxy-5-(hydroxymethyl)tetrahydrofuran-2-yl)pyridin-1-ium (2R (β) nicotinamide riboside) chloride comprising providing a crystalline 3-carbamoyl-1-((2R,3R,4S,5R)-3,4-dihydroxy-5-(hydroxymethyl)tetrahydrofuran-2-yl)pyridin-1-ium (2R (β) nicotinamide riboside) chloride, and contacting the crystalline 2R (β) nicotinamide riboside chloride with water.

20. A method of treating a disease or disorder that would benefit from increased NAD levels comprising administering a pharmaceutical composition of claim 17.

* * * * *